(12) United States Patent
Matty

(10) Patent No.: US 10,001,771 B2
(45) Date of Patent: Jun. 19, 2018

(54) SYSTEMS AND METHODS FOR TRACKING TEETH MOVEMENT DURING ORTHODONTIC TREATMENT

(71) Applicant: Align Technology, Inc., San Jose, CA (US)

(72) Inventor: Rick Matty, Scotts Valley, CA (US)

(73) Assignee: Align Technology, Inc., San Jose, CA (US)

( * ) Notice: Subject to any disclaimer, the term of this patent is extended or adjusted under 35 U.S.C. 154(b) by 8 days.

(21) Appl. No.: 14/815,006

(22) Filed: Jul. 31, 2015

(65) Prior Publication Data
US 2015/0338844 A1    Nov. 26, 2015

Related U.S. Application Data

(62) Division of application No. 13/194,802, filed on Jul. 29, 2011, now Pat. No. 9,125,709.

(51) Int. Cl.
*A61C 8/00* (2006.01)
*G05B 19/4097* (2006.01)
(Continued)

(52) U.S. Cl.
CPC .......... *G05B 19/4097* (2013.01); *A61C 7/002* (2013.01); *A61C 7/08* (2013.01);
(Continued)

(58) Field of Classification Search
CPC .. A61C 7/002; A61C 7/08; A61C 7/14; G05B 19/4097; G05B 2219/45244; B33Y 80/00
See application file for complete search history.

(56) References Cited

U.S. PATENT DOCUMENTS 2,467,432 A    4/1949   Kesling
3,407,500 A    10/1968  Kesling
(Continued)

FOREIGN PATENT DOCUMENTS

AU    3031677 A    5/1979
AU     517102 B2   7/1981
(Continued)

OTHER PUBLICATIONS

AADR. American Association for Dental Research, Summary of Activities, Mar. 20-23, 1980, Los ngeles, CA, p. 195.
(Continued)

*Primary Examiner* — Heidi M Eide
(74) *Attorney, Agent, or Firm* — Wilson Sonsini Goodrich & Rosati

(57) ABSTRACT

Methods, systems, and apparatus's for improving orthodontic treatments. In an embodiment, an orthodontic tracking template is provided for assisting in determining whether a patient's teeth are in an appropriate tooth arrangement for transitioning between a wire and bracket orthodontic treatment to a patient-removable orthodontic appliance treatment. The tracking template may include a shell portion defining a plurality of tooth-receiving cavities arranged to fit over at least a portion of the patient's teeth in an intermediate tooth arrangement without applying a tooth-moving force to the teeth or to any brackets attached to the teeth.

20 Claims, 14 Drawing Sheets

(51) Int. Cl.
*A61C 7/00* (2006.01)
*A61C 7/08* (2006.01)
*A61C 7/14* (2006.01)
*B33Y 80/00* (2015.01)

(52) U.S. Cl.
CPC .................. *A61C 7/14* (2013.01); *B33Y 80/00* (2014.12); *G05B 2219/45244* (2013.01)

(56) References Cited

U.S. PATENT DOCUMENTS

| | | |
|---|---|---|
| 3,600,808 A | 8/1971 | Reeve |
| 3,660,900 A | 5/1972 | Andrews |
| 3,683,502 A | 8/1972 | Wallshein |
| 3,738,005 A | 6/1973 | Cohen |
| 3,860,803 A | 1/1975 | Levine |
| 3,916,526 A | 11/1975 | Schudy |
| 3,922,786 A | 12/1975 | Lavin |
| 3,950,851 A | 4/1976 | Bergersen |
| 3,983,628 A | 10/1976 | Acevedo |
| 4,014,096 A | 3/1977 | Dellinger |
| 4,195,046 A | 3/1980 | Kesling |
| 4,253,828 A | 3/1981 | Coles et al. |
| 4,324,546 A | 4/1982 | Heitlinger et al. |
| 4,324,547 A | 4/1982 | Arcan et al. |
| 4,348,178 A | 9/1982 | Kurz |
| 4,478,580 A | 10/1984 | Barrut |
| 4,500,294 A | 2/1985 | Lewis |
| 4,504,225 A | 3/1985 | Yoshii |
| 4,505,673 A | 3/1985 | Yoshii |
| 4,526,540 A | 7/1985 | Dellinger |
| 4,575,330 A | 3/1986 | Hull |
| 4,575,805 A | 3/1986 | Moermann et al. |
| 4,591,341 A | 5/1986 | Andrews |
| 4,609,349 A | 9/1986 | Cain |
| 4,611,288 A | 9/1986 | Duret et al. |
| 4,656,860 A | 4/1987 | Orthuber et al. |
| 4,663,720 A | 5/1987 | Duret et al. |
| 4,664,626 A | 5/1987 | Kesling |
| 4,676,747 A | 6/1987 | Kesling |
| 4,742,464 A | 5/1988 | Duret et al. |
| 4,755,139 A | 7/1988 | Abbatte et al. |
| 4,763,791 A | 8/1988 | Halverson et al. |
| 4,793,803 A | 12/1988 | Martz |
| 4,798,534 A | 1/1989 | Breads |
| 4,836,778 A | 6/1989 | Baumrind et al. |
| 4,837,732 A | 6/1989 | Brandestini et al. |
| 4,850,864 A | 7/1989 | Diamond |
| 4,850,865 A | 7/1989 | Napolitano |
| 4,856,991 A | 8/1989 | Breads et al. |
| 4,877,398 A | 10/1989 | Kesling |
| 4,880,380 A | 11/1989 | Martz |
| 4,889,238 A | 12/1989 | Batchelor |
| 4,890,608 A | 1/1990 | Steer |
| 4,935,635 A | 6/1990 | O'Harra |
| 4,936,862 A | 6/1990 | Walker et al. |
| 4,937,928 A | 7/1990 | van der Zel |
| 4,941,826 A | 7/1990 | Loran et al. |
| 4,964,770 A | 10/1990 | Steinbichler et al. |
| 4,975,052 A | 12/1990 | Spencer et al. |
| 4,983,334 A | 1/1991 | Adell |
| 5,011,405 A | 4/1991 | Lemchen |
| 5,017,133 A | 5/1991 | Miura |
| 5,027,281 A | 6/1991 | Rekow et al. |
| 5,035,613 A | 7/1991 | Breads et al. |
| 5,055,039 A | 10/1991 | Abbatte et al. |
| 5,059,118 A | 10/1991 | Breads et al. |
| 5,100,316 A | 3/1992 | Wildman |
| 5,121,333 A | 6/1992 | Riley et al. |
| 5,125,832 A | 6/1992 | Kesling |
| 5,128,870 A | 7/1992 | Erdman et al. |
| 5,130,064 A | 7/1992 | Smalley |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,176,517 A | 1/1993 | Truax |
| 5,184,306 A | 2/1993 | Erdman et al. |
| 5,186,623 A | 2/1993 | Breads et al. |
| 5,257,203 A | 10/1993 | Riley et al. |
| 5,273,429 A | 12/1993 | Rekow et al. |
| 5,278,756 A | 1/1994 | Lemchen et al. |
| 5,328,362 A | 7/1994 | Watson et al. |
| 5,338,198 A | 8/1994 | Wu et al. |
| 5,340,309 A | 8/1994 | Robertson |
| 5,342,202 A | 8/1994 | Deshayes |
| 5,368,478 A | 11/1994 | Andreiko et al. |
| 5,382,164 A | 1/1995 | Stern |
| 5,395,238 A | 3/1995 | Andreiko et al. |
| 5,440,326 A | 8/1995 | Quinn |
| 5,440,496 A | 8/1995 | Andersson et al. |
| 5,447,432 A | 9/1995 | Andreiko et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,431,562 A | 11/1995 | Andreiko et al. |
| 5,474,448 A | 12/1995 | Andreiko et al. |
| RE35,169 E | 3/1996 | Lemchen et al. |
| 5,518,397 A | 5/1996 | Andreiko et al. |
| 5,528,735 A | 6/1996 | Strasnick et al. |
| 5,533,895 A | 7/1996 | Andreiko et al. |
| 5,542,842 A | 8/1996 | Andreiko et al. |
| 5,549,476 A | 8/1996 | Stern |
| 5,562,448 A | 10/1996 | Mushabac |
| 5,587,912 A | 12/1996 | Andersson et al. |
| 5,605,459 A | 2/1997 | Kuroda et al. |
| 5,607,305 A | 3/1997 | Andersson et al. |
| 5,614,075 A | 3/1997 | Andre |
| 5,621,648 A | 4/1997 | Crump |
| 5,645,420 A | 7/1997 | Bergersen |
| 5,645,421 A | 7/1997 | Slootsky |
| 5,655,653 A | 8/1997 | Chester |
| 5,683,243 A | 11/1997 | Andreiko et al. |
| 5,692,894 A | 12/1997 | Schwartz et al. |
| 5,725,376 A | 3/1998 | Poirier |
| 5,725,378 A | 3/1998 | Wang |
| 5,733,126 A | 3/1998 | Andersson et al. |
| 5,740,267 A | 4/1998 | Echerer et al. |
| 5,742,700 A | 4/1998 | Yoon et al. |
| 5,799,100 A | 8/1998 | Clarke et al. |
| 5,800,174 A | 9/1998 | Andersson |
| 5,823,778 A | 10/1998 | Schmitt et al. |
| 5,848,115 A | 12/1998 | Little et al. |
| 5,857,853 A | 1/1999 | van Nifterick et al. |
| 5,866,058 A | 2/1999 | Batchelder et al. |
| 5,879,158 A | 3/1999 | Doyle et al. |
| 5,880,961 A | 3/1999 | Crump |
| 5,880,962 A | 3/1999 | Andersson et al. |
| 5,934,288 A | 8/1999 | Avila et al. |
| 5,957,686 A | 9/1999 | Anthony |
| 5,964,587 A | 10/1999 | Sato |
| 5,971,754 A | 10/1999 | Sondhi et al. |
| 5,975,893 A | 11/1999 | Chishti et al. |
| 6,015,289 A | 1/2000 | Andreiko et al. |
| 6,044,309 A | 3/2000 | Honda |
| 6,049,743 A | 4/2000 | Baba |
| 6,062,861 A | 5/2000 | Andersson |
| 6,068,482 A | 5/2000 | Snow |
| 6,099,314 A | 8/2000 | Kopelman et al. |
| 6,123,544 A | 9/2000 | Cleary |
| 6,152,731 A | 11/2000 | Jordon et al. |
| 6,183,248 B1 | 2/2001 | Chishti et al. |
| 6,190,165 B1 | 2/2001 | Andreiko et al. |
| 6,217,325 B1 | 4/2001 | Chishti et al. |
| 6,217,334 B1 | 4/2001 | Hultgren |
| 6,244,861 B1 | 6/2001 | Andreiko et al. |
| 6,299,440 B1 * | 10/2001 | Phan ............... A61C 7/08 433/18 |
| 6,309,215 B1 * | 10/2001 | Phan ............... A61C 7/00 433/24 |
| 6,315,553 B1 | 11/2001 | Sachdeva et al. |
| 6,322,359 B1 | 11/2001 | Jordan et al. |
| 6,350,120 B1 | 2/2002 | Sachdeva et al. |
| 6,382,975 B1 | 5/2002 | Poirier |

(56) References Cited

U.S. PATENT DOCUMENTS

| | | | |
|---|---|---|---|
| 6,398,548 | B1 | 6/2002 | Muhammad et al. |
| 6,402,707 | B1 | 6/2002 | Ernst |
| 6,482,298 | B1 | 11/2002 | Bhatnagar |
| 6,524,101 | B1 | 2/2003 | Phan et al. |
| 6,554,611 | B2 | 4/2003 | Chishti et al. |
| 6,572,372 | B1 | 6/2003 | Phan et al. |
| 6,629,840 | B2 | 10/2003 | Chishti et al. |
| 6,705,863 | B2 | 3/2004 | Phan et al. |
| 6,722,880 | B2 | 4/2004 | Chishti et al. |
| 9,125,709 | B2 | 9/2015 | Matty |
| 2002/0006597 | A1 | 1/2002 | Andreiko et al. |
| 2003/0009252 | A1 | 1/2003 | Pavlovskaia et al. |
| 2003/0139834 | A1 | 7/2003 | Nikolskiy et al. |
| 2003/0186184 | A1 | 10/2003 | Chishti et al. |
| 2003/0219691 | A1 | 11/2003 | Phan et al. |
| 2003/0224311 | A1 | 12/2003 | Cronauer |
| 2004/0128010 | A1 | 7/2004 | Pavlovskaia et al. |
| 2005/0026102 | A1 | 2/2005 | Miller |
| 2005/0055118 | A1 | 3/2005 | Nikolskiy et al. |
| 2005/0106525 | A1 | 5/2005 | Knopp et al. |
| 2005/0233276 | A1* | 10/2005 | Kopelman ............... A61C 7/08 433/3 |
| 2006/0199141 | A1* | 9/2006 | Wen .......................... A61C 7/08 433/24 |
| 2008/0294405 | A1* | 11/2008 | Kitching ................... A61C 7/08 703/11 |
| 2008/0306724 | A1 | 12/2008 | Kitching et al. |
| 2010/0151404 | A1 | 6/2010 | Wu et al. |
| 2010/0167225 | A1* | 7/2010 | Kuo .......................... A61C 7/08 433/24 |
| 2010/0239992 | A1 | 9/2010 | Brandt et al. |
| 2012/0260924 | A1* | 10/2012 | Foster .................. A63B 71/085 128/861 |
| 2013/0029283 | A1 | 1/2013 | Matty |

FOREIGN PATENT DOCUMENTS

| | | |
|---|---|---|
| AU | 5598894 A | 6/1994 |
| CA | 1121955 | 4/1982 |
| DE | 2749802 | 5/1978 |
| DE | 69327661 T | 7/2000 |
| EP | 0091876 A1 | 10/1983 |
| EP | 0299490 A2 | 1/1989 |
| EP | 0376873 A2 | 7/1990 |
| EP | 0490848 A2 | 6/1992 |
| EP | 0541500 A1 | 5/1993 |
| EP | 0667753 B1 | 8/1995 |
| EP | 0731673 B1 | 9/1996 |
| EP | 0774933 B1 | 5/1997 |
| ES | 463897 | 1/1980 |
| FR | 2369828 A1 | 6/1978 |
| FR | 2652256 A1 | 3/1991 |
| GB | 15500777 | 8/1979 |
| JP | 53-058191 | 5/1978 |
| JP | 04-028359 | 1/1992 |
| JP | 08-508174 | 9/1996 |
| WO | WO 90/08512 A1 | 8/1990 |
| WO | WO 91/04713 A1 | 4/1991 |
| WO | WO 94/10935 A1 | 5/1994 |
| WO | WO 98/32394 A1 | 7/1998 |
| WO | WO 98/44865 A1 | 10/1998 |
| WO | WO 98/58596 A1 | 12/1998 |
| WO | WO 2006/118771 A2 | 11/2006 |

OTHER PUBLICATIONS

Alcaniz, et aL, "An Advanced System for the Simulation and Planning of Orthodontic Treatments," Karl Heinz Hohne and Ron Kikinis (eds.), Visualization in Biomedical Computing, 4th Intl. Conf., VBC '96, Hamburg, Germany, Sep. 22-25, 1996, Springer-Verlag, pp. 511-520.

Alexander et al., "The DigiGraph Work Station Part 2 Clinical Management," JCO, pp. 402-407 (Jul. 1990).

Altschuler et al., "Analysis of 3-D Data for Comparative 3-D Serial Growth Pattern Studies of Oral-Facial Structures," AADR Abstracts, Program and Abstracts of Papers, 57th General Session, IADR Annual Session, Mar. 29, 1979-Apr. 1, 1979, New Orleans Marriot, Journal of Dental Research, vol. 58, Jan. 1979, Special Issue A, p. 221.

Altschuler et al., "Laser Electro-Optic System for Rapid Three-Dimensional (3D) Topographic Mapping of Surfaces," Optical Engineering, 20(6):953-961 (1981).

Altschuler et al., "Measuring Surfaces Space-Coded by a Laser-Projected Dot Matrix," SPIE Imaging q Applications for Automated Industrial Inspection and Assembly, vol. 182, p. 187-191 (1979).

Altschuler, "3D Mapping of Maxillo-Facial Prosthesis," AADR Abstract #607, 2 pages total, (1980).

Andersson et al., "Clinical Results with Titanium Crowns Fabricated with Machine Duplication and Spark Erosion," Acta. Odontol. Scand., 47:279-286 (1989).

Andrews, The Six Keys to Optimal Occlusion Straight Wire, Chapter 3, pp. 13-24 (1989).

Bartels, et al., An Introduction to Splines for Use in Computer Graphics and Geometric Modeling, Morgan Kaufmann Publishers, pp. 422-425 (1987).

Baumrind et al., "A Stereophotogrammetric System for the Detection of Prosthesis Loosening in Total Hip Arthroplasty," NATO Symposium on Applications of Human Biostereometrics, Jul. 9-13, 1978, SPIE, vol. 166, pp. 112-123.

Baumrind et al., "Mapping the Skull in 3-D," reprinted from J. Calif. Dent. Assoc., 48(2), 11 pages total, (1972 Fall Issue).

Baumrind, "A System for Craniofacial Mapping Through the Integration of Data from Stereo X-Ray Films and Stereo Photographs," an invited paper submitted to the 1975 American Society of Photogram Symposium on Close-Range Photogram Systems, University of III., Aug. 26-30, 1975, pp. 142-166.

Baumrind, "Integrated Three-Dimensional Craniofacial Mapping: Background, Principles, and Perspectives," Semin. in Orthod., 7(4):223-232 (Dec. 2001).

Begole et al., "A Computer System for the Analysis of Dental Casts," The Angle Orthod., 51(3):253-259 (Jul. 1981).

Bernard et al.,"Computerized Diagnosis in Orthodontics for Epidemiological Studies: A ProgressReport," Abstract, J. Dental Res. Special Issue, vol. 67, p. 169, paper presented at International Association for Dental Research 66th General Session, Mar. 9-13, 1988, Montreal, Canada.

Bhatia et al., "A Computer-Aided Design for Orthognathic Surgery," Br. J. Oral Maxillofac. Surg., 22:237-253 (1984).

Biggerstaff et al., "Computerized Analysis of Occlusion in the Postcanine Dentition," Am. J. Orthod., 61(3): 245-254 (Mar. 1972).

Biggerstaff, "Computerized Diagnostic Setups and Simulations," Angle Orthod., 40(1):28-36 (Jan. 1970).

Biostar Operation & Training Manual. Great Lakes Orthodontics, Ltd. 199 Fire Tower Drive,Tonawanda, New York. 14150-5890, 20 pages total (1990).

Blu, et al., "Linear interpolation revitalized", IEEE Trans. Image Proc., 13(5):710-719 (May 2004).

Bourke, "Coordinate System Transformation," (Jun. 1996), p. 1, retrieved from the Internet Nov. 5, 2004, URL <http://astronomy.swin.edu.au/—pbourke/prolection/coords>.

Boyd et al., "Three Dimensional Diagnosis and Orthodontic Treatment of Complex Malocclusions With the Invisalipn Appliance," Semin. Orthod., 7(4):274-293 (Dec. 2001).

Brandestini et al., "Computer Machined Ceramic Inlays: In Vitro Marginal Adaptation," J. Dent. Res. Special Issue, Abstract 305, vol. 64, p. 208 (1985).

Brook et al., "An Image Analysis System for the Determination of Tooth Dimensions from Study Casts: Comparison with Manual Measurements of Mesio-distal Diameter," J. Dent. Res., 65(3):428-431 (Mar. 1986).

Burstone (interview), "Dr. Charles J. Burstone on the Uses of the Computer in Orthodontic Practice (Part 1)," J. Clin. Orthod., 13(7):442-453 (Jul. 1979).

Burstone (interview), "Dr. Charles J. Burstone on the Uses of the Computer in Orthodontic Practice (Part 2)," J. Clin. Orthod., 13(8):539-551 (Aug. 1979).

(56) References Cited

OTHER PUBLICATIONS

Burstone et al., Precision Adjustment of the Transpalatal Lingual Arch: Computer Arch Form Predetermination, Am, Journal of Orthodontics, vol. 79, No. 2 (Feb. 1981), pp. 115-133.
Cardinal Industrial Finishes, Powder Coatings information posted at <http://www.cardinalpaint.com> on Aug. 25, 2000, 2 pages.
Carnaghan, "An Alternative to Holograms for the Portrayal of Human Teeth," 4th Int'l. Conf. on Holographic Systems, Components and Applications, Sep. 15, 1993, pp. 228-231.
Chaconas et al., "The DigiGraph Work Station, Part 1, Basic Concepts," JCO, pp. 360-367 (Jun. 1990).
Chafetz et al., "Subsidence of the Femoral Prosthesis, A Stereophotogrammetric Evaluation," Clin. Orthop. Relat. Res., No. 201, pp. 60-67 (Dec. 1985).
Chiappone, (1980). Constructing the Gnathologic Setup and Positioner, J. Clin. Orthod, vol. 14, pp. 121-133.
Cottingham, (1969). Gnathologic Clear Plastic Positioner, Am. J. Orthod, vol. 55, pp. 23-31.
Crawford, "CAD/CAM in the Dental Office: Does It Work?", Canadian Dental Journal, vol. 57, No. 2, pp. 121-123 (Feb. 1991).
Crawford, "Computers in Dentistry: Part 1: CAD/CAM: The Computer Moves Chairside," "Part 2: F. Duret—A Man With a Vision," "Part 3: The Computer Gives New Vision—Literally," "Part 4: Bytes 'N Bites" The Computer Moves From the Front Desk to the Operatoiy, Canadian Dental Journal, vol. 54(9), pp. 661-666 (1988).
Crooks, "CAD/CAM Comes to USC," USC Dentistry, pp. 14-17 (Spring 1990).
Cureton, Correcting Malaligned Mandibular Incisors with Removable Retainers, J.Clin. Orthod, vol. 30, No. 7 (1996) pp. 390-395.
Curry et al., "Integrated Three-Dimensional Craniofacial Mapping at the Craniofacial Research Instrumentation Laboratory/University of the Pacific," Semin. Orthod., 7(4):258-265 (Dec. 2001).
Cutting et al., "Three-Dimensional Computer-Assisted Design of Craniofacial Surgical Procedures: Optimization and Interaction with Cephalometric and CT-Based Models," Plast. 77(6):877-885 (Jun. 1986).
DCS Dental AG, "The CAD/CAM 'DCS Titan System' for Production of Crowns/Bridges," DSC Production, pp. 1-7 (Jan. 1992.
Definition for gingiva. Dictionary.com p. 1-3. Retrieved from the internet Nov. 5, 2004 <http://reference.com/search/search?q=gingiva>.
DeFranco et al., "Three-Dimensional Large Displacement Analysis of Orthodontic Appliances," J. Biomechanics, 9:793-801 (1976).
Dental Institute University of Zurich Switzerland, Program for International Symposium on Computer Restorations: State of the Art of the CEREC-Method, May 1991, 2 pages total.
Dentrac Corporation, Dentrac document, pp. 4-13 (1992).
DENT-X posted on Sep. 24, 1998 at <http://www.dent-x.com/DentSim.htm>, 6 pages.
Doyle, "Digital Dentistry," Computer Graphics World, pp. 50-52, 54 (Oct. 2000).
DuraClearTM product information, Allesee Orthodontic Appliances-Pro Lab, 1 page (1997).
Duret et al, "CAD-CAM in Dentistry," J. Am. Dent. Assoc. 117:715-720 (Nov. 1988).
Duret et al., "CAD/CAM Imaging in Dentistry," Curr. Opin. Dent., 1:150-154 (1991).
Duret, "The Dental CAD/CAM, General Description of the Project," Hennson International Product Brochure, 18 pages total, Jan. 1986.
Duret,"Vers Une Prosthese Informatisee," (English translation attached), Tonus, vol. 75, pp. 55-57 (Nov. 15, 1985).
Economides, "The Microcomputer in the Orthodontic Office," JCO, pp. 767-772 (Nov. 1979).
Elsasser, Some Observations on the History and Uses of the Kesling Positioner, Am. J. Orthod. (1950) 36:368-374.
English translation of Japanese Laid-Open Publication No. 63-11148 to inventor T. Ozukuri (Laid-Open on Jan. 18, 1998) pp. 1-7.
Felton et al., "A Computerized Analysis of the Shape and Stability of Mandibular Arch Form," Am. J. Orthod. Dentofacial Orthop., 92(6):478-483 (Dec. 1987).
Friede et al., "Accuracy of Cephalometric Prediction in Orthognathic Surgery," Abstract of Papers, J. Dent. Res., 70:754-760 (1987).
Futterling et al., "Automated Finite Element Modeling of a Human Mandible with Dental Implants," JS WSCG '98—Conference Program, retrieved from the Internet: <http://wscg.zcu.cz/wscg98/papers98/Strasser 98.pdf, 8 pages.
Gao et al., "3-D element Generation for Multi-Connected Complex Dental and Mandibular Structure," Proc. Intl Workshop on Medical Imaging and Augmented Reality, pp. 267-271 (Jun. 12, 2001).
GIM-ALLDENT Deutschland, "Das DUX System: Die Technik," 2 pages total (2002).
Gottleib et al., "JCO Interviews Dr. James A. McNamura, Jr., on the Frankel Appliance: Part 2: Clinical 1-1 Management," J. Clin. Orthod., 16(6):390-407 (Jun. 1982).
Grayson, "New Methods for Three Dimensional Analysis of Craniofacial Deformity, Symposium: Computerized Facial Imaging in Oral and Maxiiofacial Surgery," AAOMS, 3 pages total, (Sep. 13, 1990).
Guess et al., "Computer Treatment Estimates in Orthodontics and Orthognathic Surgery," JCO, pp. 262-228 (Apr. 1989).
Heaven et al. "Computer-Based Image Analysis of Artificial Root Surface Caries," Abstracts of Papers, J. Dent. Res., 70:528 (Apr. 17-21, 1991).
Highbeam Research, "Simulating Stress Put on Jaw," Tooling & Production [online], Nov. 1996, n pp. 1-2, retrieved from the Internet on Nov. 5, 2004, URL http://static.highbeam.com/t/toolingampproduction/november011996/simulatingst ressputonfa . . . >.
Hikage, "Integrated Orthodontic Management System for Virtual Three-Dimensional Computer Graphic Simulation and Optical Video Image Database for Diagnosis and Treatment Planning", Journal of Japan KA Orthodontic Society, Feb. 1987, English translation, pp. 1-38, Japanese version, 46(2), pp. 248-269 (60 pages total).
Hoffmann, et al., "Role of Cephalometry for Planning of Jaw Orthopedics and Jaw Surgery Procedures," (Article Summary in English, article in German), Informatbnen, pp. 375-396 (Mar. 1991).
Hojjatie et al., "Three-Dimensional Finite Element Analysis of Glass-Ceramic Dental Crowns," J. Biomech., 23(11):1157-1166 (1990).
Huckins, "CAD-CAM Generated Mandibular Model Prototype from MRI Data," AAOMS, p. 96 (1999).
Important Tip About Wearing the Red White & Blue Active Clear Retainer System, Allesee Orthodontic Appliances-Pro Lab, 1 p. 1998).
JCO Interviews, Craig Andreiko , DDS, MS on the Elan and Orthos Systems, JCO, pp. 459-468 (Aug. 1994).
JCO Interviews, Dr. Homer W. Phillips on Computers in Orthodontic Practice, Part 2, JCO. 1997; 1983:819-831.
Jerrold, "The Problem, Electronic Data Transmission and the Law," AJO-DO, pp. 478-479 (Apr. 1988).
Jones et al., "An Assessment of the Fit of a Parabolic Curve to Pre- and Post-Treatment Dental Arches," Br. J. Orthod., 16:85-93 (1989).
JP Faber et al., "Computerized Interactive Orthodontic Treatment Planning," Am. J. Orthod., 73(1):36-46 (Jan. 1978).
Kamada et.al., Case Reports on Tooth Positioners Using LTV Vinyl Silicone Rubber, J. Nihon University School of Dentistry (1984) 26(1): 11-29.
Kamada et.al., Construction of Tooth Positioners with LTV Vinyl Silicone Rubber and Some Case KJ Reports, J. Nihon University School of Dentistry (1982) 24(1):1-27.
Kanazawa et al., "Three-Dimensional Measurements of the Occlusal Surfaces of Upper Molars in a Dutch Population," J. Dent Res., 63(11):1298-1301 (Nov. 1984).
Kesling et al., The Philosophy of the Tooth Positioning Appliance, American Journal of Orthodontics and Oral surgery. 1945; 31:297-304.

(56) References Cited

OTHER PUBLICATIONS

Kesling, Coordinating the Predetermined Pattern and Tooth Positioner with Conventional Treatment, Am. J. Orthod. Oral Surg. (1946) 32:285-293.
Kleeman et al., The Speed Positioner, J. Clin. Orthod. (1996) 30:673-680.
Kochanek, "Interpolating Splines with Local Tension, Continuity and Bias Control," Computer Graphics, 18(3):33-41 (Jul. 1984). Oral Surgery (1945) 31 :297-30.
Kunii et al., "Articulation Simulation for an Intelligent Dental Care System," Displays 15:181-188 (1994).
Kuroda et al., Three-Dimensional Dental Cast Analyzing System Using Laser Scanning, Am. J. Orthod. Dentofac. Orthop. (1996) 110:365-369.
Laurendeau, et al., "A Computer-Vision Technique for the Acquisition and Processing of 3-D Profiles of 7 Dental Imprints: An Application in Orthodontics," IEEE Transactions on Medical Imaging, 10(3):453-461 (Sep. 1991).
Leinfelder, et al., "A New Method for Generating Ceramic Restorations: a CAD-CAM System," J. Am. 1-1 Dent. Assoc., 118(6):703-707 (Jun. 1989).
Manetti, et al., "Computer-Aided Cefalometry and New Mechanics in Orthodontics," (Article Summary in English, article in German), Fortschr Kieferorthop. 44, 370-376 (Nr. 5), 1983.
McCann, "Inside the ADA," J. Amer. Dent. Assoc., 118:286-294 (Mar. 1989).
McNamara et al., "Invisible Retainers," J. Cfin. Orthod., pp. 570-578 (Aug. 1985).
McNamara et al., Orthodontic and Orthopedic Treatment in the Mixed Dentition, Needham Press, pp. 347-353 (Jan. 1993).
Moermann et al., "Computer Machined Adhesive Porcelain Inlays: Margin Adaptation after Fatigue Stress," IADR Abstract 339, J. Dent. Res., 66(a):763 (1987).
Moles, "Correcting Mild Malalignments—As Easy As One, Two, Three," AOA/Pro Corner, vol. 11, No. 1, 2 pages (2002).
Mormann et al., "Marginale Adaptation von adhasuven Porzellaninlays in vitro," Separatdruck aus:Schweiz. Mschr. Zahnmed. 95: 1118-1129, 1985.
Nahoum, "The Vacuum Formed Dental Contour Appliance," N. Y. State Dent. J., 30(9):385-390 (Nov. 1964).
Nash, "CEREC CAD/CAM Inlays: Aesthetics and Durability in a Single Appointment," Dent. Today, 9(8):20, 22-23 (Oct. 1990).
Nishiyama et al., "A New Construction of Tooth Repositioner by LTV Vinyl Silicone Rubber," J. Nihon Univ. Sch. Dent., 19(2):93-102 (1977).
Paul et al., "Digital Documentation of Individual Human Jaw and Tooth Forms for Applications in Orthodontics, Oral Surgery and Forensic Medicine" Proc. of the 24th Annual Conf. of the IEEE Industrial Electronics Society (IECON '98), Sep. 4, 1998, pp. 2415-2418.
Pinkham, "Foolish Concept Propels Technology," Dentist, 3 pages total, Jan./Feb. 1989.
Pinkham, "Inventor's CAD/CAM May Transform Dentistry," Dentist, 3 pages total, Sep. 1990.
Ponitz, "Invisible Retainers," Am. J. Orthod., 59(3):266-272 (Mar. 1971).
PROCERA Research Projects, "PROCERA Research Projects 1993—Abstract Collection," pp. 3-7 28 (1993).
Proffit et al., Contemporary Orthodontics, (Second Ed.), Chapter 15, Mosby Inc., pp. 470-533 (Oct. 1993).
Raintree Essix & ARS Materials, Inc., Raintree Essix, Technical Magazine Table of contents and Essix Appliances, <http://www.essix.com/magazine/defaulthtml> Aug. 13, 1997.
Redmond et al., "Clinical Implications of Digital Orthodontics," Am. J. Orthod. Dentofacial Orthop., 117(2):240-242 (2000).
Rekow et al. "CAD/CAM for Dental Restorations—Some of the Curious Challenges," IEEE Trans. Biomed. Eng., 38(4):314-318 (Apr. 1991).

Rekow et al., "Comparison of Three Data Acquisition Techniques for 3-D Tooth Surface Mapping," Annual International Conference of the IEEE Engineering in Medicine and Biology Society, 13(1):344-345 1991.
Rekow, "A Review of the Developments in Dental CAD/CAM Systems," (contains references to Japanese efforts and content of the papers of particular interest to the clinician are indicated with a one line summary of their content in the bibliography), Curr. Opin. Dent., 2:25-33 (Jun. 1992).
Rekow, "CAD/CAM in Dentistry: A Historical Perspective and View of the Future," J. Can. Dent. Assoc., 58(4):283, 287-288 (Apr. 1992).
Rekow, "Computer-Aided Design and Manufacturing in Dentistry: A Review of the State of the Art," J. Prosthet. Dent., 58(4):512-516 (Oct. 1987).
Rekow, "Dental CAD-CAM Systems: What is the State of the Art?", J. Amer. Dent. Assoc., 122:43-48 1991.
Rekow, "Feasibility of an Automated System for Production of Dental Restorations, Ph.D. Thesis," Univ. of Minnesota, 244 pages total, Nov. 1988.
Richmond et al., "The Development of a 3D Cast Analysis System," Br. J. Orthod., 13(1):53-54 (Jan. 1986).
Richmond et al., "The Development of the PAR Index (Peer Assessment Rating): Reliability and Validity," Eur. J. Orthod., 14:125-139 (1992).
Richmond, "Recording the Dental Cast in Three Dimensions," Am. J. Orthod. Dentofacial Orthop., 92(3):199-206 (Sep. 1987).
Rudge, "Dental Arch Analysis: Arch Form, A Review of the Literature," Eur. J. Orthod., 3(4):279-284 1981.
Sakuda et al., "Integrated Information-Processing System in Clinical Orthodontics: an Approach with Use of a Computer Network System," Am. J. Orthod. Dentofacial Orthop., 101(3): 210-220 (Mar. 1992).
Schellhas et al., "Three-Dimensional Computed Tomography in Maxillofacial Surgical Planning," Arch. Otolamp!. Head Neck Surg., 114:438-442 (Apr. 1988).
Schroeder et al., Eds. The Visual Toolkit, Prentice Hall PTR, New Jersey (1998) Chapters 6, 8 & 9, (pp. 153-210,309-354, and 355-428, respectively).
Shilliday, (1971). Minimizing finishing problems with the mini-positioner, Am. J. Orthod. 59:596-599.
Siemens, "CEREC—Computer-Reconstruction," High Tech in der Zahnmedizin, 14 pages total (2004).
Sinclair, "The Readers' Corner," J. Clin. Orthod., 26(6):369-372 (Jun. 1992).
Sirona Dental Systems GmbH, CEREC 3D, Manuel utiiisateur, Version 2.0X (in French), 2003,114 pages total.
Stoll et al., "Computer-aided Technologies in Dentistry," (article summary in English, article in German), Dtsch Zahna'rztl Z 45, pp. 314-322 (1990).
Sturman, "Interactive Keyframe Animation of 3-D Articulated Models," Proceedings Graphics Interface '84, May-Jun. 1984, pp. 35-40.
The Choice Is Clear: Red, White & Blue . . . The Simple, Affordable, No-Braces Treatment, Allesee Orthodontic Appliances-Pro Lab product information for doctors. http://ormco.com/aoa/appliances-services/RWB/doctorhtml>, 5 pages (May 19, 2003).
The Choice is Clear: Red, White & Blue . . . The Simple, Affordable, No-Braces Treatment, Allesee Orthodontic Appliances-Pro Lab product information for patients, <http://ormco.com/aoa/appliancesservices/RWB/patients.html>, 2 pages (May 19, 2003).
The Choice Is Clear: Red, White & Blue . . . The Simple, Affordable, No-Braces Treatment, Allesee Orthodontic Appliances-Pro Lab product information, 6 pages (2003).
The Red, White & Blue Way to Improve Your Smile! Allesee Orthodontic Appliances-Pro Lab product information for patients, 2 pages 1992.
Truax L., "Truax Clasp-Less(TM) Appliance System," Funct. Orthod., 9(5):22-4, 26-8 (Sep.-Oct. 1992).
Tru-Tain Orthodontic & Dental Supplies, Product Brochure, Rochester, Minnesota 55902, 16 pages total (1996).

(56) References Cited

OTHER PUBLICATIONS

U.S. Department of Commerce, National Technical Information Service, "Automated Crown Replication Using Solid Photography SM," Solid Photography Inc., Melville NY, Oct. 1977, 20 pages total.
U.S. Department of Commerce, National Technical Information Service, "Holodontography: An Introduction to Dental Laser Holography," School of Aerospace Medicine Brooks AFB Tex, Mar. 1973, 37 pages total.
U.S. Appl. No. 60/050,342, filed Jun. 20, 1997, 41 pages total.
Van Der Linden et al., "Three-Dimensional Analysis of Dental Casts by Means of the Optocom," J. Dent. Res., p. 1100 (Jul.-Aug. 1972).
Van Der Linden, "A New Method to Determine Tooth Positions and Dental Arch Dimensions," J. Dent. Res., 51(4):1104 (Jul.-Aug. 1972).
Van Der Zel, "Ceramic-Fused-to-Metal Restorations with a New CAD/CAM System," Quintessence Int., 24(11):769-778 (1993).
Varady et al., "Reverse Engineering of Geometric Models—An Introduction," Computer-Aided Design, 29(4):255-268,1997.
Verstreken et al., "An Image-Guided Planning System for Endosseous Oral Implants," IEEE Trans. Med. Imaging, 17(5):842-852 (Oct. 1998).
Warunek et al., Physical and Mechanical Properties of Elastomers in Orthodonic Positioners, Am J. Orthod. Dentofac. Orthop, vol. 95, No. 5, (May 1989) pp. 399-400.
Warunek et.al., Clinical Use of Silicone Elastomer Applicances, JCO (1989) XXIII(10):694-700.
Wells, Application of the Positioner Appliance in Orthodontic Treatment, Am. J. Orthodont. (1970) 58:351-366.
Williams, "Dentistry and CAD/CAM: Another French Revolution," J. Dent. Practice Admin., pp. 2-5 (Jan./Mar. 1987).
Williams, "The Switzerland and Minnesota Developments in CAD/CAM," J. Dent. Practice Admin., pp. 50-55 (Apr./Jun. 1987).
Wishan, "New Advances in Personal Computer Applications for Cephalometric Analysis, Growth Prediction, Surgical Treatment Planning and Imaging Processing," Symposium: Computerized Facial Imaging in Oral and Maxilofacial Surgery Presented on Sep. 13, 1990.
WSCG'98—Conference Program, "The Sixth International Conference in Central Europe on Computer Graphics and Visualization '98," Feb. 9-13, 1998, pp. 1-7, retrieved from the Internet on Nov. 5, 2004, URL<http://wscg.zcu.cz/wscg98/wscg98.h>.
Xia et al., "Three-Dimensional Virtual-Reality Surgical Planning and Soft-Tissue Prediction for Orthognathic Surgery," IEEE Trans. Inf. Technol. Biomed., 5(2):97-107 (Jun. 2001).
Yamamoto et al., "Optical Measurement of Dental Cast Profile and Application to Analysis of Three-Dimensional Tooth Movement in Orthodontics," Front. Med. Biol. Eng., 1(2):119-130 (1988).
Yamamoto et al., "Three-Dimensional Measurement of Dental Cast Profiles and Its Applications to Orthodontics," Conf. Proc. IEEE Eng. Med. Biol. Soc., 12(5):2051-2053 (1990).
Yamany et al., "A System for Human Jaw Modeling Using Intra-Oral Images," Proc. of the 20th Annual Conf. of the IEEE Engineering in Medicine and Biology Society, Nov. 1, 1998, vol. 2, pp. 563-566.
Yoshii, "Research on a New Orthodontic Appliance: The Dynamic Positioner (D.P.); I. The D.P. Concept and Implementation of Transparent Silicone Resin (Orthocon)," Nippon Dental Review, 452:61-74 (Jun. 1980).
Yoshii, "Research on a New Orthodontic Appliance: The Dynamic Positioner (D.P.); II. The D.P. Manufacturing Procedure and Clinical Applications," Nippon Dental Review, 454:107-130 (Aug. 1980).
Yoshii, "Research on a New Orthodontic Appliance: The Dynamic Positioner (D.P.); III.—The General Concept of the D.P. Method and Its Therapeutic Effect, Part 2. Skeletal Reversed Occlusion Case Reports," Nippon Dental Review, 458:112-129 (Dec. 1980).
Yoshii, "Research on a New Orthodontic Appliance: The Dynamic Positioner (D.P.); III. The General Concept of the D.P. Method and Its Therapeutic Effect, Part 1, Dental and Functional Reversed Occlusion Case Reports," Nippon Dental Review, 457:146-164 (Nov. 1980).
You May Be a Candidate for This Invisible No-Braces Treatment, Allesee Orthodontic Appliances-Pro Lab product information for patients, 2 pages (2002).

\* cited by examiner

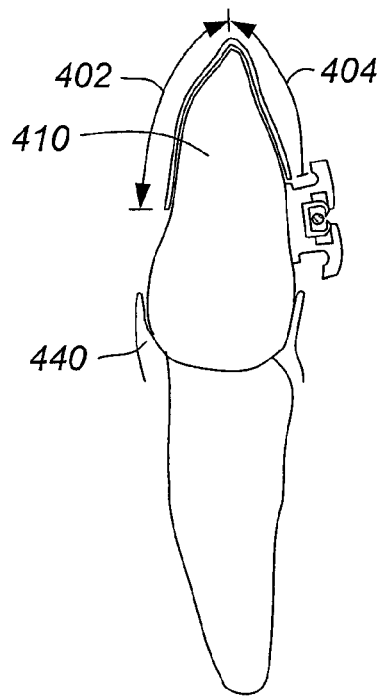
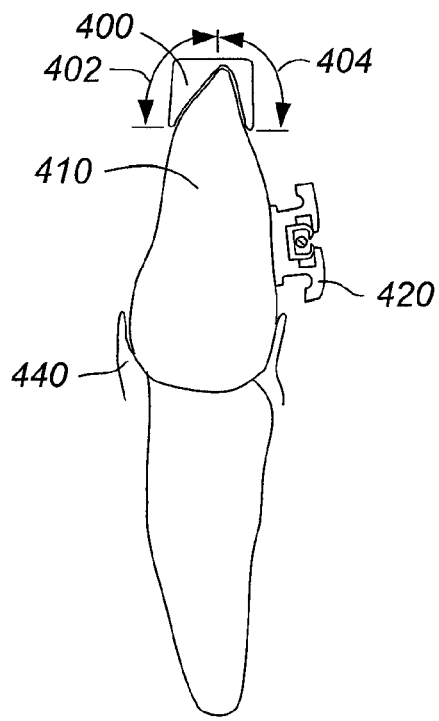
FIG. 4E  FIG. 4F
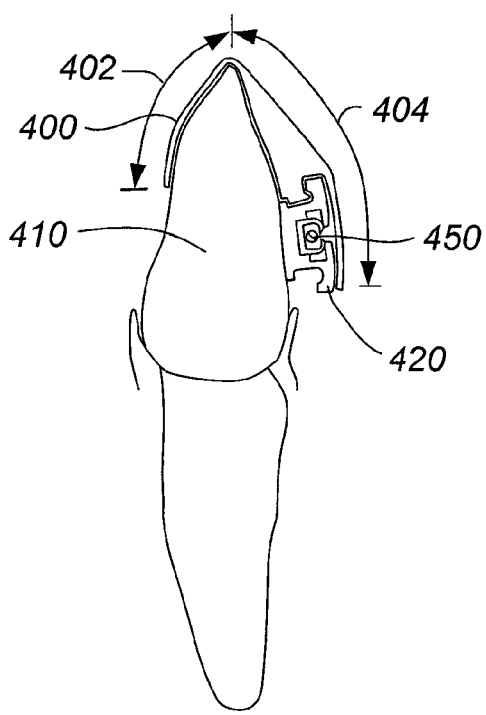
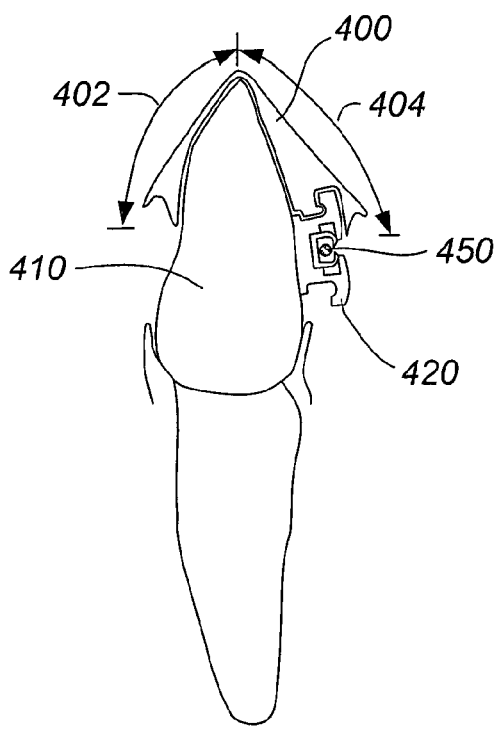
FIG. 4G  FIG. 4H

SYSTEMS AND METHODS FOR TRACKING TEETH MOVEMENT DURING ORTHODONTIC TREATMENT

CROSS-REFERENCE

This application is a divisional application of Ser. No. 13/194,802, filed Jul. 29, 2011, now U.S. Pat. No. 9,125,709, the disclosure of which is incorporated herein by reference in its entirety.

BACKGROUND

The present invention generally relates to the field of orthodontics, and more particularly to orthodontic appliances, such as shell appliances, and orthodontic tracking templates for determining when shell appliances may be applied after a wire-and-bracket treatment.

An objective of orthodontics is to move a patient's teeth to positions where function and/or aesthetics are optimized. Traditional affixed braces (i.e., a wire and brackets) exert a diminishing force on the teeth to gradually urge them toward desired positions. Over time and with a series of clinical visits, the orthodontist reactively adjusts the braces to establish new diminishing forces and move the teeth toward an acceptable final destination. In recent years, orthodontists may use wire and bracket planning software, such as Insignia, which is available from Ormco Corp. in Orange, Calif., where the planning software utilizes virtual 3D models of a patient's teeth, a wire, and brackets to assist in designing a desired virtual final tooth arrangement—no intermediate tooth arrangements.

Alternatives to conventional wire-and-bracket treatments became available in the late 1990s. For example, systems including a series of preformed patient-removable clear shell-shaped orthodontic appliances have become commercially available from Align Technology, Inc., Santa Clara, Calif., under the trade name Invisalign® System. An Invisalign® System appliance can be made from thin clear plastic and have tooth-receiving cavities. In use, the appliance is placed over the patient's teeth and typically removed after 2 weeks. Shell-shaped orthodontic appliances are designed to impart predetermined positioning or repositioning forces to the patient's teeth to obtain desired results. The imparted forces are resilient in nature and are associated with corresponding appliance elastic deformation. When used to reposition teeth, a series of individual appliances are worn by a patient to elastically reposition the patient's teeth over time. When used to retain teeth, one or more identical appliances are worn to restrain a patient's teeth in their current arrangement. The design of the shell-shaped appliances can rely on computer modeling of a series of planned successive tooth arrangements, and the individual appliances may be designed to be worn over the teeth and elastically reposition the teeth to each of the planned intermediate and final tooth arrangements.

Various deficiencies are known for wire-and-bracket treatments and patient-removable orthodontic appliance treatments. Accordingly, it is desirable to overcome such deficiencies when wire-and-bracket treatments and patient-removable orthodontic appliance treatments are performed in isolation.

BRIEF SUMMARY

The present invention provides methods, systems, and apparatus's for using both traditional wire and affixed appliances (e.g., brackets) and a series of preformed patient-removable orthodontic appliances (e.g., Invisalign® appliances).

Methods and structures including an orthodontic tracking template and template fabrication are provided. The tracking template includes a shell or shell portion having defining one or more tooth-receiving cavities shaped to fit over at least a portion of a plurality of teeth in a planned tooth arrangement (e.g., a planned target or intermediate arrangement). The tracking template can be shaped or configured to fit over at least a portion of the teeth of the patient as the patient is wearing at least one affixed appliance (e.g., a bracket for use in a bracket-and-wire treatment) without applying a tooth-moving force to the at least one affixed appliance.

Methods and systems for orthodontic treatment and/or treatment planning are provided. The system includes at least one affixed appliance (e.g., a bracket for use in a bracket-and-wire treatment) worn by the patient by attachment to at least one of a plurality of teeth, and an orthodontic tracking template. The template can include a shell or shell portion defining one or more tooth-receiving cavities arranged to fit over at least a portion of the plurality of teeth in a planned intermediate tooth arrangement without applying a tooth-moving force to the at least one affixed appliance. The system may further include at least one patient-removable orthodontic tooth positioning appliance having a shell portion defining a plurality of tooth-receiving cavities shaped to receive and apply a force (e.g., a repositioning force) to the plurality of teeth.

For a fuller understanding of the nature and advantages of the present invention, reference should be made to the ensuing detailed description and accompanying drawings. Other aspects, objects and advantages of the invention will be apparent from the drawings and detailed description that follows.

BRIEF DESCRIPTION OF THE DRAWINGS

FIG. 4E illustrates a fifth embodiment of a tooth-receiving cavity adapted to fit a tooth and an affixed appliance.

FIG. 4F illustrates a sixth embodiment of a tooth-receiving cavity adapted to fit a tooth and an affixed appliance.

FIG. 4G illustrates a seventh embodiment of a tooth-receiving cavity adapted to fit a tooth and an affixed appliance.

FIG. 4H illustrates an eighth embodiment of a tooth-receiving cavity adapted to fit a tooth and an affixed appliance.

DETAILED DESCRIPTION

Embodiments of the present invention provide methods, systems, and apparatus's for orthodontic treatment and positioning of a patient's teeth utilizing a wire and affixed appliances (e.g., a wire and brackets) and at least one patient-removable orthodontic appliance (e.g., a patient-removable shell appliance).

Figure 1:
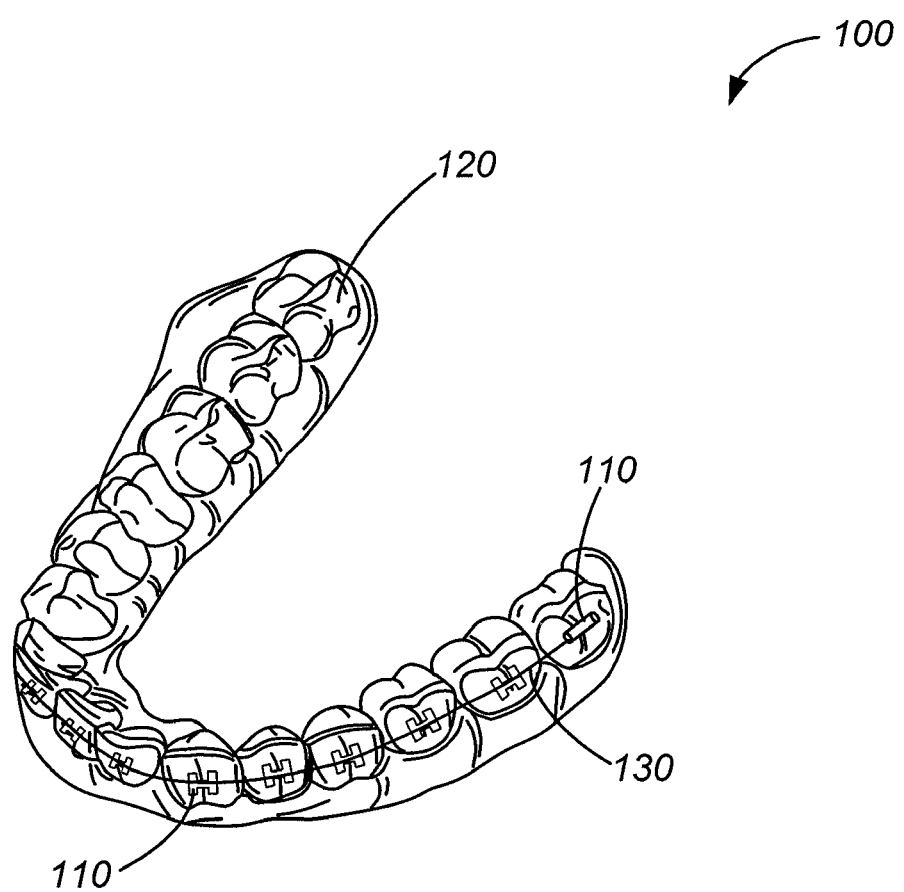
FIG. 1 shows a lower jaw with a plurality of affixed appliances attached to a lingual or facial surface of the teeth and a wire mechanically coupled to the plurality of affixed appliances.

In general, a patient may wish to pursue a treatment plan where the patient in at least one phase of the treatment plan receives a wire and affixed appliances such as a wire and brackets (e.g., those illustrated in FIG. 1). Treatment may further include or utilize, e.g., in another phase of the treatment plan, patient-removable orthodontic appliances such as shell-shaped orthodontic appliances designed to impart positioning or repositioning forces to the patient's teeth (e.g., that illustrated in FIG. 2). Treatment may optionally include use of both a wire and affixed appliance and shell appliance(s), or only a single type of such appliances. A selected treatment can include any combination of such appliances in any conceivable order, or any series of alternating appliance types.

The overall goal of the orthodontic treatment may be to reposition a patient's teeth from an initial tooth arrangement to a planned arrangement, such as an intermediate or final tooth arrangement. The bracket-and-wire treatment may be designed to reposition the teeth from the initial tooth arrangement to the planned intermediate tooth arrangement. The planned intermediate tooth arrangement may be pre-planned or predetermined in the sense that it may be determined prior to beginning treatment. However, the intermediate tooth arrangement may also be determined at other times during the phase in which a wire and affixed appliances are applied; for example, during a phase of the treatment plan in which a wire and affixed appliances are applied, the planned intermediate tooth arrangement may be modified in accordance with changing needs or a patient's changing desires. In a typical case, the intermediate tooth arrangement will be pre-planned and predetermined (i.e., prior to beginning treatment) using treatment planning software running on a digital computer.

The patient-removable orthodontic appliance treatment may be designed to reposition the patient's teeth from any planned intermediate tooth arrangement to a planned final tooth arrangement. For example, the patient-removable orthodontic appliance treatment may take over where the bracket-and-wire treatment ends such that the patient's teeth are repositioned from a planned intermediate tooth arrangement to a planned final arrangement. The planned final tooth arrangement may be pre-planned or predetermined similar to the planned intermediate tooth arrangement. Like the planned intermediate tooth arrangement, the final tooth arrangement may also be determined at times other than before treatment begins. In a typical case, however, the final tooth arrangement will be pre-planned and predetermined (i.e., prior to beginning treatment) using treatment planning software running on a digital computer.

When applying the bracket-and-wire treatment, it may be desirable to determine whether the doctor has made the correct reactive adjustments during treatment to obtain the planned intermediate tooth arrangement. Such a determination may indicate whether the patient is ready to transition from the bracket-and-wire treatment to the patient-removable orthodontic appliance treatment.

According to some embodiments, an impression of the teeth with the brackets and wire may be taken to determine whether the patient's teeth have been positioned into the intermediate tooth arrangement. According to other embodiments, the teeth may be scanned to determine whether they have been positioned into the intermediate tooth arrangement.

According to yet other embodiments, it may be desirable to determine whether the teeth are arranged into the intermediate tooth arrangement without taking an impression or scan. To do so, a tracking template may be designed to fit the teeth if the teeth are substantially positioned into the intermediate tooth arrangement. For example, tooth-receiving cavities in the template may be arranged to fit the teeth if the teeth are substantially arranged in the intermediate tooth arrangement without applying a tooth-moving force to the plurality of teeth. To address the provision of a wire and/or affixed appliances, the tracking template may be adapted to also fit any such wire and/or affixed appliances without applying a tooth-moving force to the affixed appliances and without interfering with the wire. As a result, the tracking template may be applied to a patient's teeth during a bracket-and-wire treatment without removing the wire or affixed appliances. If the tracking template fits the teeth, it may be determined that the teeth are substantially positioned into the planned intermediate tooth treatment, the brackets and wire may be removed, and a patient-removable orthodontic appliance treatment may begin. On the other hand, if the tracking template does not fit, it may be determined that the teeth are not yet positioned into the planned intermediate tooth treatment, and the bracket-and-wire treatment may continue.

Embodiments of the present invention may advantageously result in any or all of the following: a smooth transition from a treatment plan using affixed appliances to a treatment plan using patient-removable orthodontic appliances; an increase in the quality of fit between a patient's tooth arrangement at the end of a treatment plan using affixed appliances and a first patient-removable orthodontic appliance; a smooth transition to a treatment plan using patient-removable orthodontic appliances without requiring an impression or scan to be taken during a treatment plan using affixed appliances; and a determination of whether a patient's teeth are ready for a treatment plan using patient-removable orthodontic appliances without requiring removal of affixed appliances; determination of what teeth need to be moved to create a smooth transition.

FIG. 1 shows a lower jaw 100 with a plurality of affixed appliances 110 attached to a lingual or facial surface of the teeth 120 and a wire 130 mechanically coupled to the plurality of affixed appliances. Affixed appliances 110 and wire 130 generally serve to cause one or more of teeth 120 to move in accordance with a treatment plan. In some cases, only certain teeth will be repositioned while other teeth can provide a base or anchor region for holding the wire in place as it applies force against the tooth or teeth targeted for repositioning. In some cases, many or most, and even all, of the teeth will be repositioned at some point during treatment. Teeth which are engaged can also serve as a base or anchor for holding the wire.

The plurality of affixed appliances may include brackets for holding or supporting a wire, orthodontic separators (i.e., spacers), coil springs (e.g., a small spring placed around an archwire to either maintain or increase space between teeth), tubes, bands (e.g., a ring surrounding an anchor molar tooth in the back of the mouth), ties (e.g., for holding a wire in place), ligature ties (e.g., a very thin wire wrapped around a bracket holding the archwire into its slot), expansion appliances (e.g., an appliance placed in the palate used to widen the arch), hooks (e.g., a part of the bracket or band used for attachment of rubber bands), microchips (e.g., an electronic device that measures the forces that act on a bracket and subsequently, a tooth interface), etc. The affixed appliances 110 may be made of any suitable material. For example, they may be made of metal, metal alloys, plated metals, ceramic, plastic, rubber, etc.

The plurality of affixed appliances 110 may be provided on any surface of the teeth. For example, they may be provided on a lingual or facial surface of the teeth, a lingual surface of the teeth, a contact surface of the teeth, etc. In some embodiments, affixed appliances 110 may be provided between teeth. The affixed appliances 110 may be provided on the teeth of any jaw. For example, they may be provided on lower jaw 100, or on an upper jaw. Further, the affixed appliances 110 may be provided on all of the teeth, or only on one or more of the teeth. In some embodiments, the affixed appliances 110 also include means for affixing the appliances to the teeth, such as adhesives, bonding agents, dental cement, etc.

The wire 130 (e.g., an archwire) may be made of any suitable material. For example, wire 130 may be made of metal, metal alloys, plated metals, ceramic, plastic, rubber, temperature sensitive materials, etc. The wire 130 may be of any suitable length. For example, wire 130 may extend across all of the teeth 120 in a jaw, or may extend only across some of the teeth 120 in a jaw. In some embodiments, no wire is provided.

Figure 2:
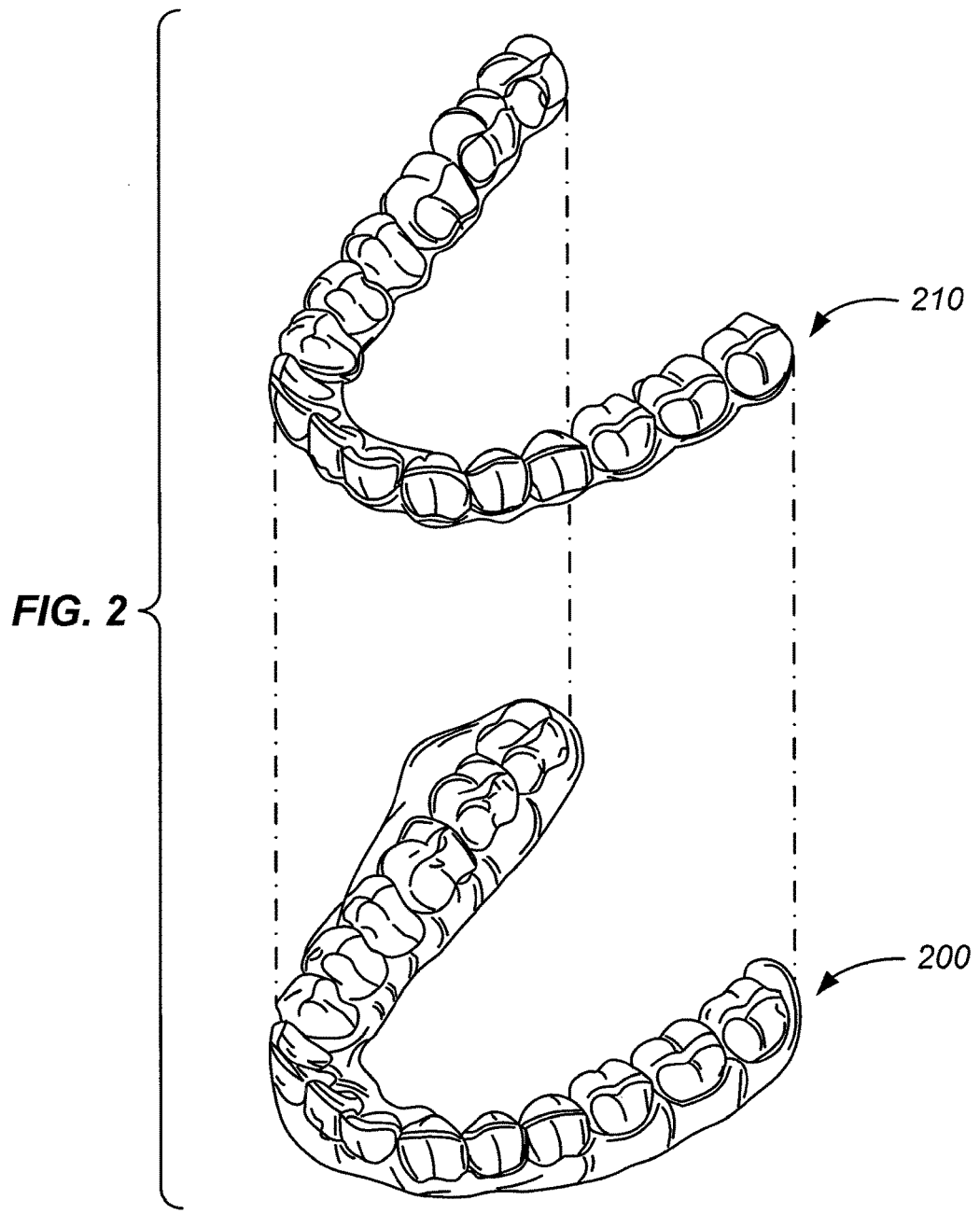
FIG. 2 shows a lower jaw and a patient-removable orthodontic tooth positioning appliance.

FIG. 2 shows a lower jaw 200 and a patient-removable orthodontic tooth positioning appliance 210. Appliance 210 is worn by a patient in order to restrain and/or reposition the patient's teeth (e.g., teeth as illustrated in jaw 200). The appliance may comprise a shell (e.g., a polymeric shell) or a shell portion defining a plurality of tooth-receiving cavities that are shaped to receive and apply a resilient positioning force for restraining and/or repositioning the teeth. In one embodiment, a polymeric appliance can be formed from a thin sheet of suitable elastomeric polymeric material, such as Tru-Train (e.g., 0.03 inch) thermal forming dental material (Tru-Train Plastics, Rochester, Minn.). An appliance can fit over all teeth present in an upper or lower jaw, or less then all of the teeth. In some cases, only certain teeth received by an appliance will be repositioned by the appliance while other teeth can provide a base or anchor region for holding the appliance in place as it applies force against the tooth or teeth targeted for repositioning. In some cases, many or most, and even all, of the teeth will be repositioned at some point during treatment. Teeth which are engaged can also serve as a base or anchor for holding the appliance as it is worn by the patient. In some instances, no wires or other means will be provided for holding an appliance in place over the teeth. In some cases, however, it may be desirable or necessary to provide individual anchors on teeth with corresponding receptacles or apertures in the appliance so that the appliance can apply a selected force on the tooth. Exemplary appliances, including those utilized in the Invisalign® System, are described in numerous patents and patent applications assigned to Align Technology, Inc. including, for example in U.S. Pat. Nos. 6,450,807, and 5,975,893, and U.S. patent application Ser. No. 12/633,715, all which are incorporated by reference herein in their entirety, as well as on the company's website, which is accessible on the World Wide Web (see, e.g., the url "align.com").

An appliance can be designed and/or provided as part of a set or plurality of appliances. Each appliance may be configured so a tooth-receiving cavity has a geometry corresponding to the intermediate or final tooth arrangement intended for the patient's teeth. The patient's teeth may be progressively repositioned from the planned intermediate tooth arrangement to the planned final tooth arrangement by placing a series of incremental position adjustment appliances over the patient's teeth. The adjustment appliances can be generated all at the same stage or in sets or batches, e.g., at the beginning of a stage of the treatment, and the patient wears each appliance until the pressure of each appliance on the teeth can no longer be felt or has resulted in the maximum allowable tooth movement for that given stage. A plurality of different appliances (e.g., a set) can be designed and even fabricated prior to the patient wearing any appliance of the plurality. After wearing an appliance for an appropriate period of time, the patient replaces the current appliance with the next appliance in the series until no more appliances remain. The appliances are generally not affixed to the teeth and the patient may place and replace the appliances at any time during the procedure; i.e., patient-removable appliances. The final appliance or several appliances in the series may have a geometry or geometries selected to overcorrect the tooth arrangement; i.e., have a geometry which would (if fully achieved) move individual teeth beyond the tooth arrangement which has been selected as "final." Such over-correction may be desirable in order to offset potential relapse after the repositioning method has been terminated; i.e., to permit movement of individual teeth back toward their pre-corrected positions. Over-correction may also be beneficial to speed the rate of correction; i.e., by having an appliance with a geometry that is positioned beyond a desired intermediate or final position, the individual teeth will be shifted toward the position at a greater rate. In such cases, the use of an appliance can be terminated before the teeth reach the positions defined by the appliance. In some cases, a single appliance may be used to reposition the patient's teeth from the planned intermediate tooth arrangement to the planned final tooth arrangement.

Figure 3A:
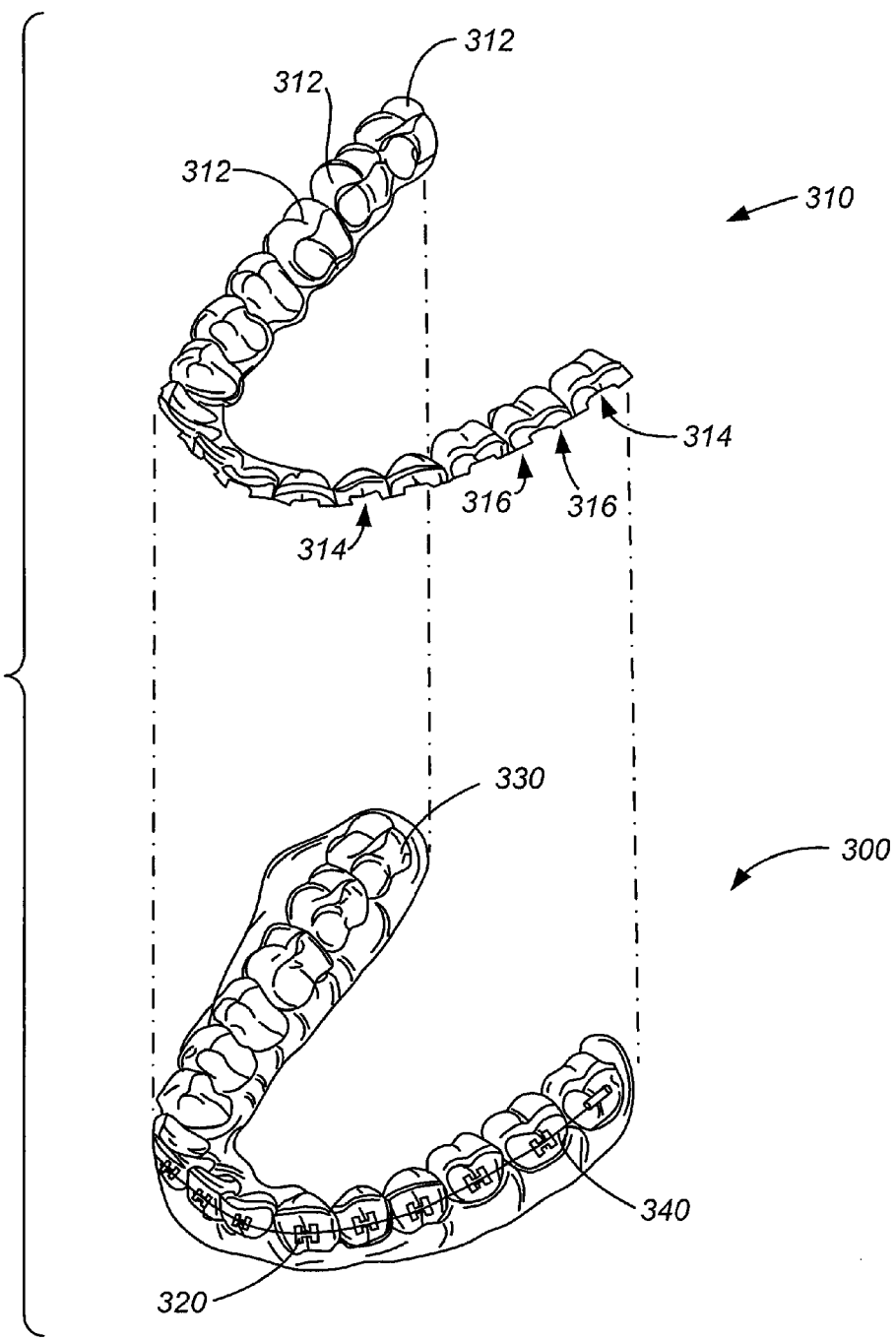
FIG. 3A shows a lower jaw and an orthodontic tracking template for use with affixed appliances attached to a lingual or facial surface of teeth and a wire mechanically coupled to the affixed appliances, according to an embodiment.

FIG. 3A shows a lower jaw 300 and an orthodontic tracking template 310 for use with affixed appliances 320 attached to a lingual or facial surface of teeth 330 and a wire 340 mechanically coupled to the affixed appliances 320, according to an embodiment. According to an embodiment, tracking template 310 includes a shell or shell portion defining a plurality of tooth-receiving cavities 312 arranged to fit over teeth 330 when teeth 330 are in the intermediate tooth arrangement. Tooth-receiving cavities 312 may each be arranged to fit over an entire tooth, or only a portion of a tooth. For example, in some embodiments, a tooth-receiving cavity may only fit over a contact surface of a tooth, a lingual surface of a tooth, a lingual or facial surface of a tooth, etc. Tracking template 310 may include a tooth-receiving cavity corresponding to each tooth in jaw 300. Alternatively, in some embodiments, tracking template 310 includes fewer tooth-receiving cavities than teeth; for example, tracking template 310 may include a number of tooth-receiving cavities less than a number of teeth in jaw 300.

In addition to being arranged to fit over teeth 330, tooth-receiving cavities 312 are also adapted to fit with affixed appliances 320. For example, as illustrated in FIG. 3, an affixed appliance 320 (e.g., a bracket) may be bonded to a lingual or facial surface of each of the plurality of teeth 330 in jaw 300. For each affixed appliance 320, a corresponding tooth-receiving cavity 312 may include an appliance-receiving surface 314 for abutting an edge of affixed appliance 320. In some embodiments, appliance-receiving surface 314 conforms to a contour of affixed appliance 320. Tooth-receiving cavities 312 may also be adapted to fit with wire 340 or other orthodontic devices mechanically coupled to affixed appliances 320. For example, as illustrated in FIG. 3, wire 340 may be mechanically coupled to affixed appliances 320. Each tooth-receiving cavity 312 may include one or more wire-receiving surfaces 316 for abutting a surface of wire 340. The wire-receiving surfaces 316 for one or more tooth-receiving cavities 312 may be in parallel with one another or offset from one another.

Regardless of whether wire 340 is mechanically coupled to affixed appliances 320, tooth-receiving cavities 312 of tracking template 310 are adapted to fit over at least a portion of the plurality of teeth 330 without applying a tooth-moving force to the plurality of teeth 330 or to the affixed appliances 320. That is, tooth-receiving cavities 312 are designed such that, when the plurality of teeth 330 are in the planned intermediate tooth arrangement, application of tracking template 310 does apply a tooth-moving force to any of teeth 330 or affixed appliances 320. A tooth-moving force is a force sufficient to cause measurable movement of a tooth when the force is applied to the tooth over a prolonged but predetermined amount of time.

In some embodiments, wire 340 is mechanically coupled to affixed appliances 320. In such embodiments, tooth-receiving cavities 312 of tracking template 310 are adapted to fit over at least a portion of the plurality of teeth 330 without interfering with wire 340. Interference with wire 340 may include displacing wire 340 or applying a force to wire 340 sufficient to cause measurement movement of a tooth when the force is applied to the wire over a prolonged but predetermined amount of time.

Figure 3B:
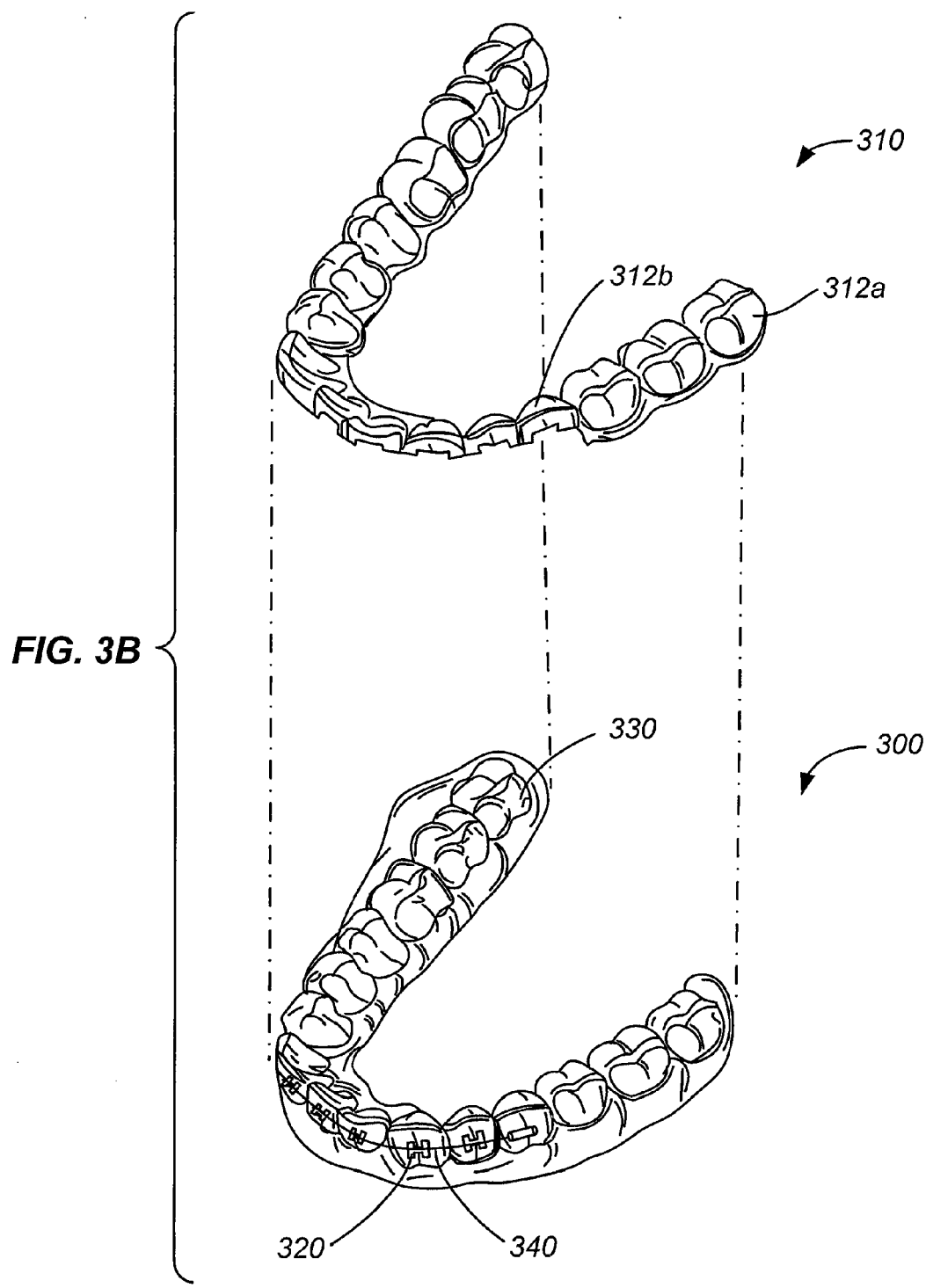
FIG. 3B shows a lower jaw and an orthodontic tracking template for use with affixed appliances attached to a lingual or facial surface of a subset of teeth and a wire mechanically coupled to the affixed appliances, according to an embodiment.

FIG. 3B shows a lower jaw 300 and an orthodontic tracking template 310 for use with affixed appliances 320 attached to a lingual or facial surface of a subset of teeth 330 and a wire 340 mechanically coupled to the affixed appliances, according to an embodiment. According to some embodiments, as illustrated in FIG. 3B, tracking template 310 includes a shell or shell portion defining a plurality of tooth-receiving cavities 312a arranged to fit entirely over one or more of teeth 330, as well as a plurality of tooth-receiving cavities 312b arranged to fit partially over one or more of teeth 330 and also adapted to fit one or more of affixed appliances 320 and wire 340. For example, one or more affixed appliances 320 may be bonded to one or more teeth 330, and a wire may be mechanically coupled to the one or more affixed appliances 320. Tracking template 310 may then include tooth-receiving cavities 312a arranged to fit entirely over one or more of teeth 330 which do not have affixed appliances 320 bonded thereto, and may also include tooth-receiving cavities 312b arranged to fit partially over one or more remaining teeth 330 and also adapted to fit over one or more affixed appliances 320 and wire 340.

Regardless of whether wire 340 is mechanically coupled to affixed appliances 320, tooth-receiving cavities 312a and 312b of tracking template 310 are adapted to fit over at least a portion of the plurality of teeth 330 without applying a tooth-moving force to the plurality of teeth 330 or to the affixed appliances 320. In some embodiments, wire 340 is mechanically coupled to affixed appliances 320. In such embodiments, tooth-receiving cavities 312a and 312b of tracking template 310 are adapted to fit over at least a portion of the plurality of teeth 330 without interfering with wire 340.

Any of teeth 330 may have affixed appliances 320 bonded thereto, and accordingly tracking template 310 may include tooth-receiving cavities adapted to fit affixed appliances 320 bonded to any tooth. For example, as illustrated in FIG. 3B, affixed appliances 320 may be attached to a patient's incisors and pre-molars. In other embodiments, affixed appliances 320 may be attached to only incisors, or only pre-molars, or only molars, or only one incisor, one pre-molar, one-molar, or any combination thereof.

Figure 3C:
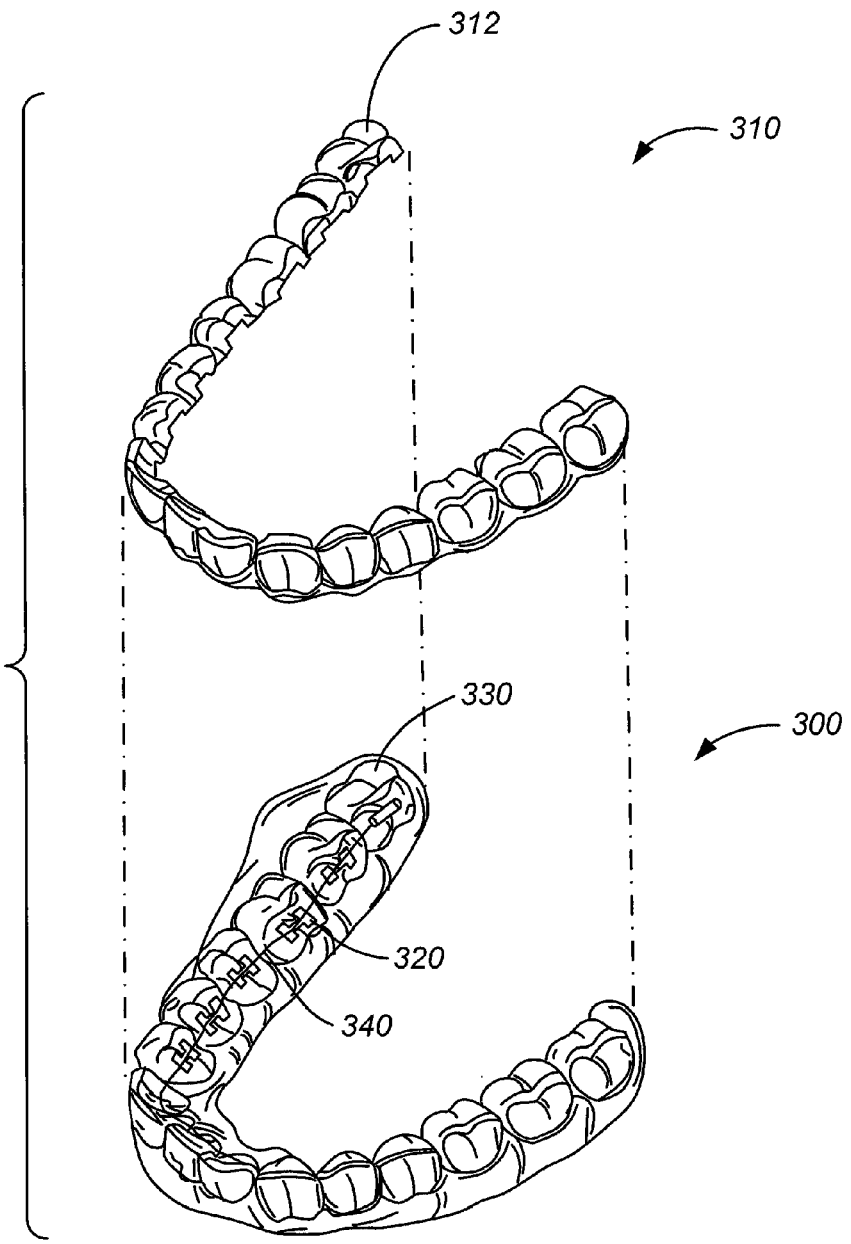
FIG. 3C shows a lower jaw and an orthodontic tracking template for use with affixed appliances attached to a lingual surface of teeth and a wire mechanically coupled to the affixed appliances, according to an embodiment.

FIG. 3C shows a lower jaw 300 and an orthodontic tracking template 310 for use with affixed appliances 320 attached to a lingual surface of teeth 330 and a wire 340 mechanically coupled to the affixed appliances, according to an embodiment. According to some embodiments, any lingual or facial (e.g., buccal or labial) surface of teeth 330 may have affixed appliances 320 bonded thereto. Thus, tooth-receiving cavities 312 of tracking template 310 may be adapted to fit affixed appliances 320 bonded to any surface of teeth 330. For example, as illustrated in FIG. 3C, affixed appliances 320 may be bonded to lingual surfaces of teeth 330. Accordingly, a surface of tooth-receiving cavities 312 corresponding to the lingual or facial surface of teeth 330 may be arranged to fit over the entire exposed lingual or facial surface of teeth 330, and a surface of tooth-receiving cavities 312 corresponding to the lingual surface of teeth 330 may be arranged to fit over only a portion of the exposed lingual surface of teeth 330. The surface of tooth-receiving cavities 312 corresponding to the lingual surface of teeth 330 may also be adapted to fit with affixed appliances 320 bonded to a lingual surface of teeth 330, similar to the fit described above with reference to FIGS. 3A and 3B.

Similar to the affixed appliances 320 and tracking template 310 described above with reference to FIG. 3B, tracking template 310 may include a shell or shell portion defining a plurality of tooth-receiving cavities arranged to fit entirely over one or more of teeth 330, as well as a plurality of tooth-receiving cavities arranged to fit partially over one or more of teeth 330 and also adapted to fit one or more of affixed appliances 320 bonded to a lingual surface of teeth 330 and mechanically coupled to wire 340. Further similar to the affixed appliances 320 and tracking template 310 described above with reference to FIG. 3B, any of teeth 330 may have affixed appliances 320 bonded to lingual surfaces thereof, and accordingly tracking template 310 may include tooth-receiving cavities adapted to fit affixed appliances 320 bonded to a lingual surface of any tooth.

FIGS. 4A to 4H illustrate various embodiments of a tooth-receiving cavity 400 defined by a shell or shell portion of a tracking template being adapted to fit a tooth 410 and an affixed appliance 420 attached to the tooth. Tooth 410 is coupled to a root 430 which is surrounded by gingiva line 440. The embodiments illustrated in FIGS. 4A to 4H are not meant to limit the scope of the invention, but rather are provided as examples for adapting a tooth-receiving cavity to fit a tooth and an affixed appliance. The tooth illustrated in FIGS. 4A to 4H may be any tooth of a plurality of teeth in either an upper jaw or a lower jaw of a patient, and the surface which affixed appliance 420 is attached to may be any lingual or facial (e.g., buccal or labial) surface of the tooth.

Figure 4A:
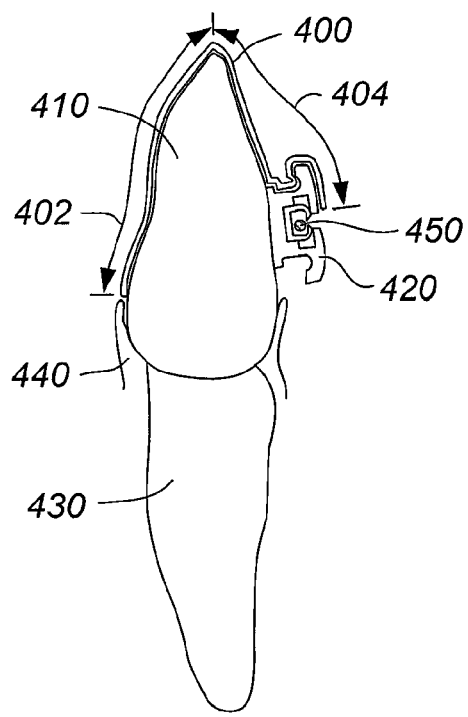
FIG. 4A illustrates a first embodiment of a tooth-receiving cavity adapted to fit a tooth and an affixed appliance.

FIG. 4A illustrates a first embodiment of a tooth-receiving cavity 400 adapted to fit a tooth 410 and an affixed appliance 420. According to this embodiment, tooth-receiving cavity 400 includes a first portion 402 which, when disposed on tooth 410, extends along a lingual surface of tooth 410 from a cusp of tooth 410 to a gingiva line 440. A root 430 is attached opposite tooth 410. First portion 402 includes a surface for contacting tooth 410 and is contoured to receive tooth 410. In some embodiments, a thickness of first portion 402 may be approximately 1 mm. In other embodiments, the thickness of first portion 402 may be larger or smaller than 1 mm, for example, the thickness of may be 0.5 mm, or 2 mm. In some embodiments, first portion 402 may contact or extend past the gingiva line 440. In other embodiments, first portion 402 does not contact or reach the gingival line 440; for example, when tooth-receiving cavity 400 is disposed over tooth 410, first portion 402 may be approximately 1 mm away from the gingiva line 440.

According to this embodiment, tooth-receiving cavity 400 also includes a second portion 404 which, when disposed on tooth 410, extends along a facial surface of tooth 410 from the cusp of tooth 410 to a wire 450 mechanically coupled to affixed appliances 420. First portion 402 is coupled to second portion 404 such that the cusp of tooth 410 may be covered by tooth-receiving cavity 400. Second portion 404 includes a surface for contacting tooth 410 and also for contacting a portion of affixed appliance 420. In this embodiment, the thickness of second portion 404 is the same as the thickness of first portion 402. Further, second portion 404 extends to a location of attachment 420 where wire 450 is mechanically coupled. For example, affixed appliance 420 may include a clasp for holding wire 450 and through which wire 450 may extend. The clasp, and thus wire 450, may be vertically disposed at the center of attachment 420. Accordingly, second portion 404 may extend to the center of attachment 420 or a location immediately before the center of attachment 420. By extending second portion 404 to a location immediately prior to wire 450, tooth-receiving cavity 400 may advantageously avoid interference with wire 450.

Figure 4B:
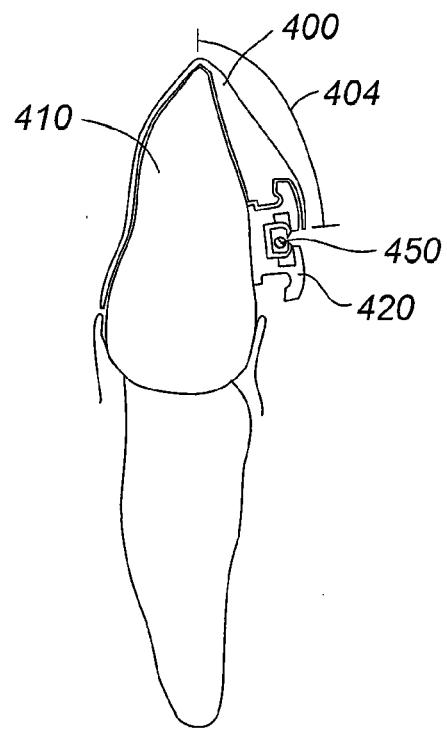
FIG. 4B illustrates a second embodiment of a tooth-receiving cavity adapted to fit a tooth and an affixed appliance.

FIG. 4B illustrates a second embodiment of a tooth-receiving cavity 400 adapted to fit a tooth 410 and an affixed appliance 420. Except where articulated, the features of this embodiment are the same as those discussed with reference to FIG. 4A. According to this embodiment, second portion 404 has a thickness which varies as second portion 404 extends from the cusp of tooth 410. That is, the thickness of second portion 404 increases as second portion 404 extends from the cusp of tooth 410 to wire 450. Second portion 404 is adapted to substantially fill contours created by a portion of attachment 420. Accordingly, second portion 404 includes a first surface that conforms with a shape of tooth 410 and attachment 420, and a second surface that is substantially planar. By increasing a thickness of second portion 404, a resiliency to breakage of tooth-receiving cavity 400 may advantageously be increased.

Figure 4C:
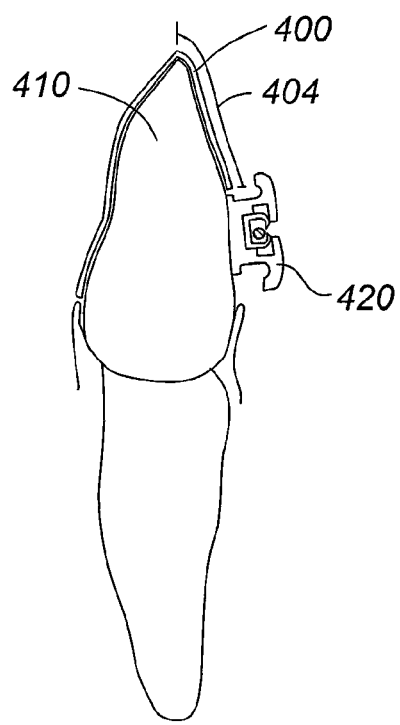
FIG. 4C illustrates a third embodiment of a tooth-receiving cavity adapted to fit a tooth and an affixed appliance.

FIG. 4C illustrates a third embodiment of a tooth-receiving cavity 400 adapted to fit a tooth 410 and an affixed appliance 420. Except where articulated, the features of this embodiment are the same as those discussed with reference to FIG. 4A. According to this embodiment, second portion 404 extends from the cusp of tooth 410 to a surface of attachment 420 that is in contact with tooth 410 and closest to the cusp of tooth 410. That is, attachment 420 includes numerous surfaces. Some of the surfaces are closer to the cusp of tooth 410 than others. Some of the surfaces are also closer to the surface of tooth 410 than others. Surfaces of attachment 420 that are proximate to a surface of tooth 410 may be referred to as being coupled to tooth 410, and may actually be coupled to tooth 410. Accordingly, second portion 404 may extend from the cusp of tooth 410 to the surface of attachment 420 which is both coupled to tooth 410 and closer to the cusp of tooth 410 than any other surfaces of attachment 420 that are coupled to tooth 410.

Figure 4D:
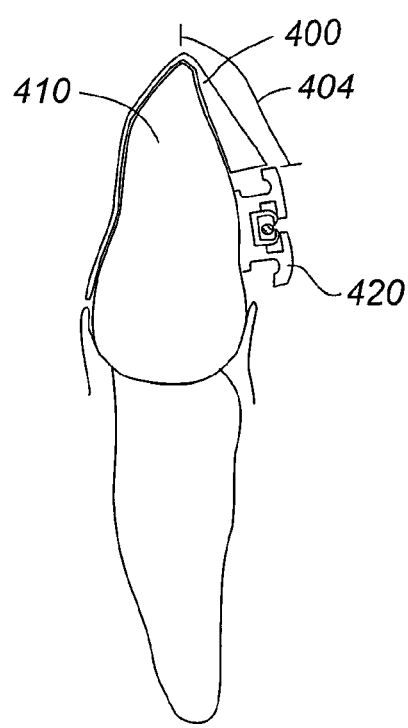
FIG. 4D illustrates a fourth embodiment of a tooth-receiving cavity adapted to fit a tooth and an affixed appliance.

FIG. 4D illustrates a fourth embodiment of a tooth-receiving cavity 400 adapted to fit a tooth 410 and an affixed appliance 420. Except where articulated, the features of this embodiment are the same as those discussed with reference to FIG. 4A. According to this embodiment, second portion 404 extends from the cusp of tooth 410 to a surface of attachment 420 that is closest to the cusp of tooth 410. That is, attachment 420 includes numerous surfaces. Some of the surfaces are closer to the cusp of tooth 410 than others, regardless of whether the surfaces are coupled to tooth 410. Accordingly, second portion 404 may extend from the cusp of tooth 410 to the surface of attachment 420 which is closer to the cusp of tooth 410 than any other surface of attachment 420. According to this embodiment, a thickness of second portion 404 varies, similar to that discussed above with reference to FIG. 4B.

FIG. 4E illustrates a fifth embodiment of a tooth-receiving cavity 400 adapted to fit a tooth 410 and an affixed appliance 420. Except where articulated, the features of this embodiment are the same as those discussed with reference to FIG. 4A. According to this embodiment, first portion 402 extends along the lingual surface of tooth 410 to a location before the gingiva line 440. For example, first portion 402 may extend along the lingual surface of tooth 410 approximately a same amount as second portion 404 extends along the facial surface of tooth 410. For another example, first portion 402 may extend to a location approximately halfway between the cusp of tooth 410 and the gingiva line 440. Extending first portion 402 a distance approximately equal to a distance which second portion 404 extends may advantageously increase an ease of manufacturing the tracking template.

FIG. 4F illustrates a sixth embodiment of a tooth-receiving cavity 400 adapted to fit a tooth 410 and an affixed appliance 420. Except where articulated, the features of this embodiment are the same as those discussed with reference to FIG. 4A. According to this embodiment, first portion 402 extends along the lingual surface of tooth 410 to a location between the cusp of tooth 410 and a surface of attachment 420 closer to the cusp of tooth 410 than any other surface of attachment 420. For example, first portion 402 may extend along the lingual surface of tooth 410 for approximately 1 mm. For another example, first portion 402 may extend along the lingual surface of tooth 410 for approximately 0.5 mm. For yet another example, first portion 402 may extend along the lingual surface of tooth 410 for less than 1 mm, or more than 1 mm. Second portion 404 extends along the facial surface of tooth 410 to a location between the cusp of tooth 410 and a surface of attachment 420 closer to the cusp of tooth 410 than any other surface of attachment 420. For example, second portion 404 may extend along the lingual surface of tooth 410 for approximately 1 mm. For another example, second portion 404 may extend along the lingual surface of tooth 410 for approximately 0.5 mm. For yet another example, second portion 404 may extend along the lingual surface of tooth 410 for less than 1 mm, or more than 1 mm. In some embodiments, first portion 402 extends along the lingual surface of tooth 410 approximately a same amount as second portion 404 extends along the facial surface of tooth 410. In other embodiments, first portion 402 and second portion 404 extend along the lingual surface and the facial surface respectively to a location approximately halfway between the cusp of tooth 410 and the aforementioned surface of attachment 420. In yet other embodiments, a thickness of first portion 402 and second portion 404 may vary. For example, a thickness of the lingual surface or facial surface may be greater at the cusp of tooth 410 than at a location located closer to gingiva line 440. According to some embodiments, one or more external surfaces of tooth-receiving cavity 400 may be substantially planar, while internal surfaces of tooth-receiving cavity 400 conform to a shape of the cusp of tooth 410. Providing a thickness of first portion 402 and second portion 404 greater at the cusp of tooth 410 than at a location located closer to gingiva line 440 may advantageously increase the resilience of tooth-receiving cavity 400 to breakage. Extending first portion 402 and second portion 404 to a location between the cusp of tooth 410 and a surface of attachment 420 closer to the cusp of tooth 410 than any other surface of attachment 420 may also advantageously increase the resilience of tooth-receiving cavity 400 to breakage and increase the ease of manufacturing the tracking template.

FIG. 4G illustrates a seventh embodiment of a tooth-receiving cavity 400 adapted to fit a tooth 410 and an affixed appliance 420. Except where articulated, the features of this embodiment are the same as those discussed with reference to FIG. 4A. According to this embodiment, first portion 402 extends along the lingual surface of tooth 410 as discussed with reference to FIG. 4E. Second portion 404 extends along the facial surface of tooth 410 past wire 450. That is, second portion 404 extends along the facial surface of tooth 410 past a location of attachment 420 where wire 450 is mechanically coupled. For example, affixed appliance 420 may include a clasp for holding wire 450 and through which wire 450 may extend. The clasp, and thus wire 450, may be vertically disposed at the center of attachment 420. Accordingly, second portion 404 may extend past the center of attachment 420. In one embodiment, second portion 404 extends to a surface of attachment 420 farther away from the cusp of tooth 410 than any other surface of attachment 420. In another embodiment, second portion 404 extends past the surface of attachment 420 farther away from the cusp of tooth 410 than any other surface of attachment 420. Further according to this embodiment, second portion has a thickness similar to that described with reference to FIG. 4B. By extending second portion 404 to a location past wire 450, an accuracy of fit between tooth-receiving cavity 400 and tooth 410 may advantageously be increased.

FIG. 4H illustrates an eighth embodiment of a tooth-receiving cavity 400 adapted to fit a tooth 410 and an affixed appliance 420. Except where articulated, the features of this embodiment are the same as those discussed with reference to FIG. 4A. According to this embodiment, first portion 402 extends along the lingual surface of tooth 410 to a location similar to that discussed with reference to FIG. 4E. Each of first portion 402 and second portion 404 16 include a protruding portion such as a clasp, hook, lever, or the like, at an end of first portion 402 and second portion 404. According to one embodiment, only one of first portion 402 and second portion 404 include the protruding portion. The protruding portion(s) may advantageously increase an ease of removing the tracking template from the patient's teeth.

Although various embodiments and examples have been described with reference to FIGS. 4A to 4H, numerous variations and combinations are within the scope of embodiments of the present invention. For example, the protruding portions discussed with reference to FIG. 4H may be used with the embodiments described with reference to FIG. 4F. For another example, the extension distance of the second portion discussed with reference to FIG. 4G may be used with the embodiments described with reference to FIG. 4H. For yet another example, although the discussions above refer to first portion 402 and second portion 404 respectively disposed over lingual and facial surfaces of tooth 410, they may respectively be disposed over facial and lingual surfaces of tooth 410.

FIGS. 5A to 5D illustrate various embodiments of a tooth-receiving cavity 500 defined by a shell or shell portion of a tracking template being adapted to fit a tooth 510 and a wire 550 mechanically coupled between two affixed appliances. Tooth 510 is coupled to a root 530 which is surrounded by gingiva line 540. The embodiments illustrated in FIGS. 5A to 5D are not meant to limit the scope of the invention, but rather are provided as examples for adapting a tooth-receiving cavity to fit a tooth and a wire. The tooth illustrated in FIGS. 5A to 5D may be any tooth of a plurality of teeth in either an upper jaw or a lower jaw of a patient, and the surface which wire 550 is adjacent to may be any lingual or facial (e.g., buccal or labial) surface of the tooth. In general, tooth-receiving cavity 500, tooth 510, root 530, and gingiva line 540 are the same as discussed above with reference to FIGS. 4A to 4H. Further, tooth-receiving cavity 500 includes a first portion 502 and a second portion 504 respectively similar to the first portion 402 and second portion 404 of tooth-receiving cavity 400 described with reference to FIGS. 4A to 4H. Variations from first portion 402 and second portion 404 are discussed below.

Figure 5A:
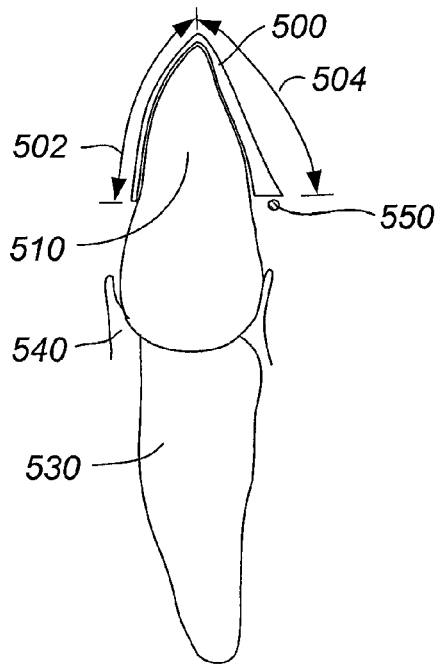
FIG. 5A illustrates a first embodiment of a tooth-receiving cavity adapted to fit a tooth and a portion of wire located between two affixed appliances.

FIG. 5A illustrates a first embodiment of a tooth-receiving cavity 500 adapted to fit a tooth 510 and a portion of wire 550 located between two affixed appliances. According to this embodiment, second portion 504 extends along facial surface of tooth 510 from the cusp of tooth 510 to a surface of wire 550 closer to the cusp of tooth 510 than any other surface of wire 550. For example, second portion 504 may extend and have a thickness such that an end of second portion 504 abuts or is proximal to wire 550. Further, a thickness of second portion 504 increases as second portion 504 extends from the cusp of tooth 510 to wire 550. In some embodiments, the thickness of second portion 504 does not increase. In some embodiments, the thickness and extension distance of first portion 502 and 504 is the same; in other embodiments, such thickness and extension distances are different. In yet other embodiments, second portion 504 extends a distance and has a thickness similar to that discussed for second portion 404 with reference to FIGS. 4A to 4F and 4H. Extending second portion 504 such that an end of second portion 504 abuts or is proximal to wire 550 may advantageously reduce interference of tooth-receiving cavity 500 with wire 550.

Figure 5B:
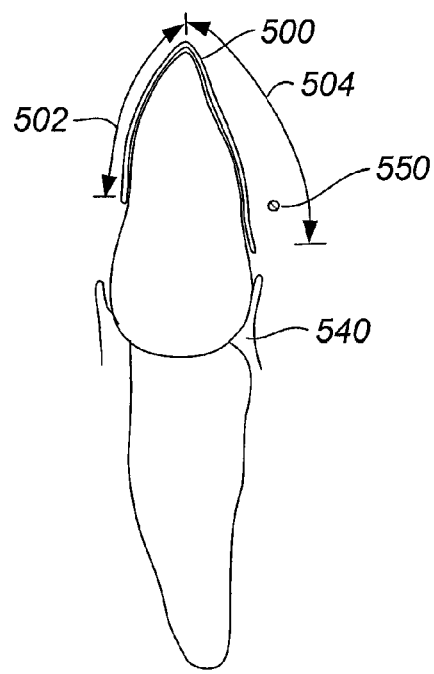
FIG. 5B illustrates a second embodiment of a tooth-receiving cavity adapted to fit a tooth and a portion of wire located between two affixed appliances.

FIG. 5B illustrates a second embodiment of a tooth-receiving cavity 500 adapted to fit a tooth 510 and a portion of wire 550 located between two affixed appliances. According to this embodiment, second portion 504 extends along the facial surface of tooth 510 from the cusp of tooth 510 past wire 550. For example, second portion 504 may extend along the facial surface to a location between wire 550 and a gingiva line 440. Further, second portion 504 extends along the facial surface of tooth 510 such that second portion 504 extends between tooth 510 and wire 550. According to one embodiment, a thickness of second portion 504 stays approximately the same as second portion 504 extends from the cusp of tooth 510 past wire 550. In some embodiments, the thickness and extension distance of first portion 502 and 504 is the same; in other embodiments, such thickness and extension distances are different. In other embodiments, second portion 504 extends a distance similar to that discussed for second portion 404 with reference to FIG. 4G. By extending second portion 504 to a location past wire 550, an accuracy of fit between tooth-receiving cavity 500 and tooth 510 may advantageously be increased.

Figure 5C:
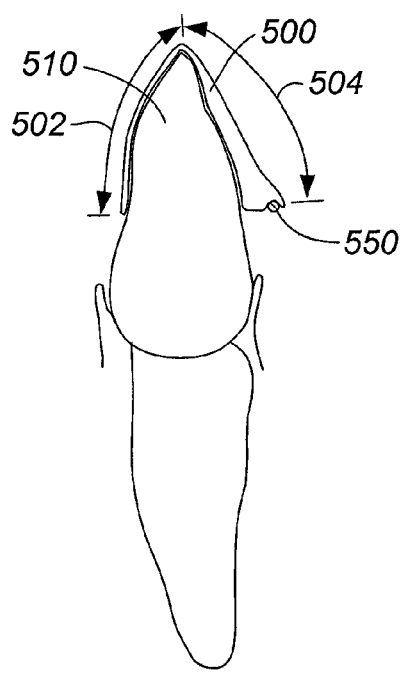
FIG. 5C illustrates a third embodiment of a tooth-receiving cavity adapted to fit a tooth and a portion of wire located between two affixed appliances.

FIG. 5C illustrates a third embodiment of a tooth-receiving cavity 500 adapted to fit a tooth 510 and a portion of wire 550 located between two affixed appliances. Except where articulated, the features of this embodiment are the same as those discussed with reference to FIG. 5A. According to this embodiment, second portion 504 extends to a location on wire 550 or past wire 550, where an end of second portion 504 includes a wire-receiving portion. Wire-receiving portion conforms to the shape of wire 550. For example, where wire 550 has a circular cross-section, wire-receiving portion may have at least a partially circular shape to conform to at least a portion of wire 550. For another example, where wire 550 has a square cross-section, wire-receiving portion may have at least a partially square shape to conform to at least a portion of wire 550. Providing an end of second portion 504 with a wire-receiving portion may advantageously reduce interference of tooth-receiving cavity 500 with wire 550.

Figure 5D:
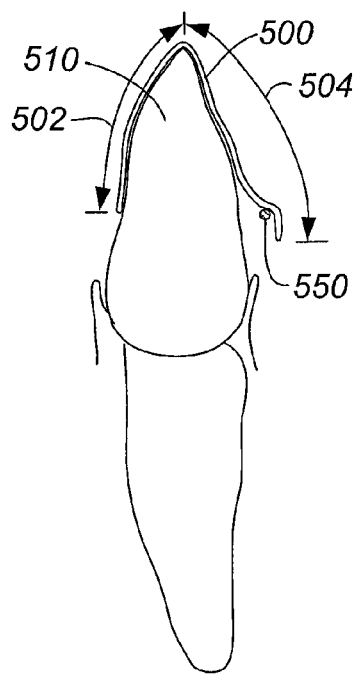
FIG. 5D illustrates a fourth embodiment of a tooth-receiving cavity adapted to fit a tooth and a portion of wire located between two affixed appliances.

FIG. 5D illustrates a fourth embodiment of a tooth-receiving cavity 500 adapted to fit a tooth 510 and a portion of wire 550 located between two affixed appliances. Except where articulated, the features of this embodiment are the same as those discussed with reference to FIG. 5B. According to this embodiment, second portion 504 extends to a location past wire 550, and extends over an outer surface of wire 550 rather than between wire 550 and tooth 510. That is, wire 550 includes a surface facing tooth 510 and a surface opposite the surface facing tooth 510. Second portion 504 may thus extend over the surface of wire 550 opposite the surface of wire 550 facing tooth 510. Extending second portion 504 over the outer surface of wire 550 may advantageously reduce interference of tooth-receiving cavity 500 with wire 550 during placement of the tracking appliance.

Although various embodiments and examples have been described with reference to FIGS. 5A to 5D, numerous variations and combinations are within the scope of embodiments of the present invention. For example, although the discussions above refer to first portion 502 and second portion 504 respectively disposed over lingual and facial surfaces of tooth 510, they may respectively be disposed over facial and lingual surfaces of tooth 510.

FIGS. 6A to 6E illustrate various embodiments of a tooth-receiving cavity 600 defined by a shell or shell portion of a tracking template being adapted to fit a tooth 610, an affixed appliance 620 attached to the tooth, and a wire 630 mechanically coupled to the affixed appliance 620. The embodiments illustrated in FIGS. 6A to 6E are not meant to limit the scope of the invention, but rather are provided as examples for adapting a tooth-receiving cavity to fit a tooth, an affixed appliance, and a wire mechanically coupled to the affixed appliance. The tooth illustrated in FIGS. 6A to 6E may be any tooth of a plurality of teeth in either an upper jaw or a lower jaw of a patient, and the surface which affixed appliance 620 is attached to may be any lingual or facial (e.g., buccal or labial) surface of the tooth.

Figure 6A:
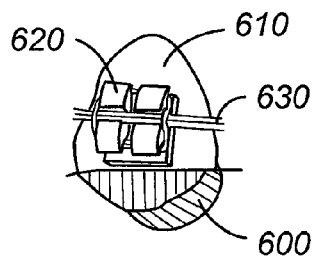
FIG. 6A illustrates a first embodiment of a tooth-receiving cavity adapted to fit a tooth, an affixed appliance, and a wire mechanically coupled to the affixed appliance.

FIG. 6A illustrates a first embodiment of a tooth-receiving cavity 600 adapted to fit a tooth 610, an affixed appliance 620, and a wire 630 mechanically coupled to the affixed appliance 620. According to this embodiment, tooth-receiving cavity 600 covers surfaces of tooth 610 extending from a cusp of tooth 610 to a location on tooth 610 where affixed appliance 620 is attached. For example, tooth-receiving cavity 600 may cover portions or all of a facial, buccal, lingual, labial, occlusal, incisal, palatal, surface, one or more cusps, one or more cingulum, one or more ridges, etc. An edge of tooth-receiving cavity 600 closest to affixed appliance 620 may be substantially planar and may not contact affixed appliance 620 when tooth-receiving cavity 600 is disposed over tooth 610. According to this embodiment, tooth-receiving cavity 600 does not cover or come into contact with wire 630. However, a portion of tooth-receiving cavity 600 may abut a portion of affixed appliance 620. Forming tooth-receiving cavity 600 such that the edge of tooth-receiving cavity 600 closest to affixed appliance 620 is substantially planar may advantageously increase the ease of manufacturing the tracking template, while forming tooth-receiving cavity 600 to not cover or come into contact with affixed appliance 620 and wire 630 may advantageously reduce interference with affixed appliance 620 and wire 630.

Figure 6B:
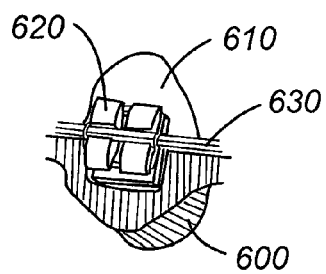
FIG. 6B illustrates a second embodiment of a tooth-receiving cavity adapted to fit a tooth, an affixed appliance, and a wire mechanically coupled to the affixed appliance.

FIG. 6B illustrates a second embodiment of a tooth-receiving cavity 600 adapted to fit a tooth 610, an affixed appliance 620, and a wire 630 mechanically coupled to the affixed appliance 620. Except where articulated, the features of this embodiment are the same as those discussed with reference to FIG. 6A. According to this embodiment, tooth-receiving cavity 600 covers surfaces of tooth 610 extending from a cusp of tooth 610 to a location on tooth 610 proximate to wire 630. An edge of tooth-receiving cavity 600 closest to affixed appliance 620 may be contoured to the shape of affixed appliance 620 such that tooth-receiving cavity 600 is formed around affixed appliance 620 but not over affixed appliance 620. Accordingly, tooth-receiving cavity 600 may abut edges of affixed appliance 620. Further, while tooth-receiving cavity 600 extends to a location on tooth 610 proximate to wire 630, tooth-receiving cavity 600 does not extend over wire 630. Rather, tooth-receiving cavity 600 substantially abuts wire 630 when disposed over tooth 610. Forming tooth-receiving cavity 600 such that it abuts affixed appliance 620 and wire 630 but does not extend over affixed appliance 620 or wire 630 may advantageously increase an accuracy of fit between tooth-receiving cavity 600 and tooth 610 while reducing interference with affixed appliance 620 and wire 630.

Figure 6C:
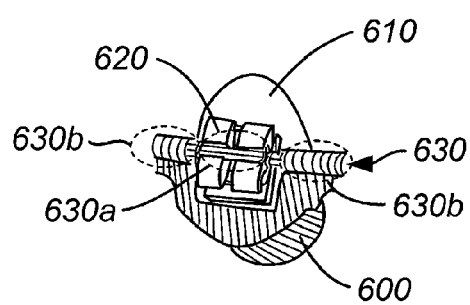
FIG. 6C illustrates a third embodiment of a tooth-receiving cavity adapted to fit a tooth, an affixed appliance, and a wire mechanically coupled to the affixed appliance.

FIG. 6C illustrates a third embodiment of a tooth-receiving cavity 600 adapted to fit a tooth 610, an affixed appliance 620, and a wire 630 mechanically coupled to the affixed appliance 620. Except where articulated, the features of this embodiment are the same as those discussed with reference to FIG. 6B. According to this embodiment, tooth-receiving cavity 600 covers surfaces of tooth 610 and wire 630. Portions of tooth-receiving cavity 600 may be contoured to the shape of wire 630 adjacent to but not passing through affixed appliance 620. For example, wire 630 may include a first portion 630*a* passing through affixed appliance 620 and one or more second portions 630*b* extending from affixed appliance 620. Tooth-receiving cavity 600 may thus include one or more portions adapted to cover one or more second portions 630*b* of wire 630. An edge of tooth-receiving cavity 600 closest to affixed appliance 620 may be contoured to the shape of affixed appliance 620 such that tooth-receiving cavity 600 is formed around affixed appliance 620 but not over affixed appliance 620. Forming tooth-receiving cavity 600 such that it covers one or more portions of wire 630 may advantageously increase an accuracy of fit between tooth-receiving cavity 600 and tooth 610 while reducing interference with affixed appliance 620.

Figure 6D:
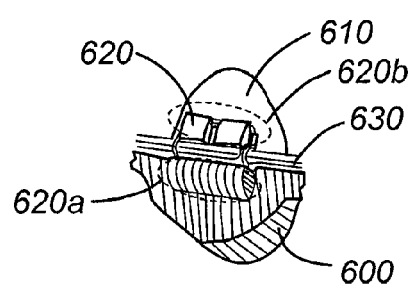
FIG. 6D illustrates a fourth embodiment of a tooth-receiving cavity adapted to fit a tooth, an affixed appliance, and a wire mechanically coupled to the affixed appliance.

FIG. 6D illustrates a fourth embodiment of a tooth-receiving cavity 600 adapted to fit a tooth 610, an affixed appliance 620, and a wire 630 mechanically coupled to the affixed appliance 620. Except where articulated, the features of this embodiment are the same as those discussed with reference to FIG. 6B. According to this embodiment, tooth-receiving cavity 600 covers surfaces of tooth 610 and affixed appliance 620 extending from a cusp of tooth 610 to a location on tooth 610 proximate to wire 630. A portion of tooth-receiving cavity 600 may be contoured to the shape of a portion of affixed appliance 620 such that tooth-receiving cavity 600 is formed over at least a portion of affixed appliance 620. For example, affixed appliance 620 may include a first portion 620*a* located between wire 630 and a cusp of tooth 610 (e.g., a contact surface of tooth 610) and a second portion 620*b* located between wire 630 and an end of tooth 610 coupled to a root of tooth 610). Tooth-receiving cavity 600 may thus include a portion adapted to cover first portion 620*a* of affixed appliance 620. An edge of tooth-receiving cavity 600 closest to wire 630 may be substantially planar. Forming tooth-receiving cavity 600 such that it covers a portion of affixed appliance 620 may advantageously increase an accuracy of fit between tooth-receiving cavity 600 and tooth 610.

Figure 6E:
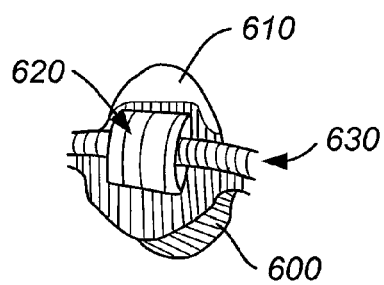
FIG. 6E illustrates a fifth embodiment of a tooth-receiving cavity adapted to fit a tooth, an affixed appliance, and a wire mechanically coupled to the affixed appliance.

FIG. 6E illustrates a fifth embodiment of a tooth-receiving cavity 600 adapted to fit a tooth 610, an affixed appliance 620, and a wire 630 mechanically coupled to the affixed appliance 620. Except where articulated, the features of this embodiment are the same as those discussed with reference to FIGS. 6C and 6D. According to this embodiment, tooth-receiving cavity 600 covers surfaces of tooth 610, affixed appliance 620, and wire 630. Portions of tooth-receiving cavity 600 may be contoured to the shape of wire 630, and portions of tooth-receiving cavity 600 may be contoured to the shape of affixed appliance 620. Tooth-receiving cavity 600 may cover all or portions of affixed appliance 620 and wire 630. In some embodiments, tooth-receiving cavity 600 extends from a cusp of tooth 610 (e.g., a contact surface of tooth 610) to a location past affixed appliance 620 and/or wire 630. Forming tooth-receiving cavity 600 such that it covers affixed appliance 620 and wire 630 may advantageously increase an accuracy of fit between tooth-receiving cavity 600 and tooth 610.

Although various embodiments and examples have been described with reference to FIGS. 6A to 6E, numerous variations and combinations are within the scope of embodiments of the present invention. For example, tooth-receiving cavity 600 may cover portions of wire 630 as discussed with reference to FIG. 6C and may also cover only portions of affixed appliance 620 as discussed with reference to FIG. 6D. Further, numerous variations and combinations with reference to other embodiments of the present invention are also within the scope of embodiments of the present invention. For example, portions of tooth-receiving cavity 600 for disposal on a surface of tooth 610 other than the surface which affixed appliance 620 is attached to may extend to different amounts as discussed with reference to FIGS. 4A to 4H. For another example, portions of tooth-receiving cavity 600 may extend between a surface of tooth 610 and wire 630 as discussed with reference to FIG. 5B.

Figure 7:
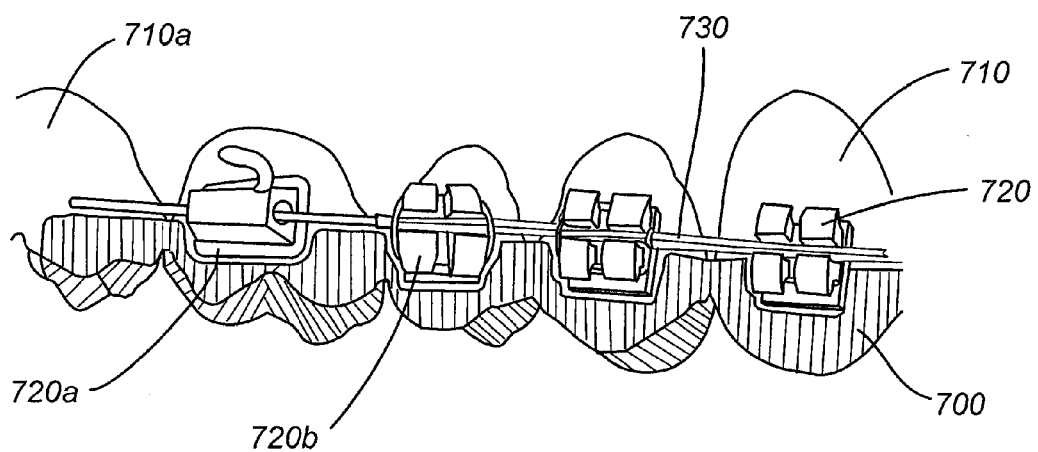
FIG. 7 shows an embodiment of a portion of a tracking template adapted to fit a plurality of teeth, a plurality of affixed appliances, and a wire mechanically coupled to the affixed appliances.

FIG. 7 shows an embodiment of a portion of a tracking template 700 adapted to fit a plurality of teeth 710, a plurality of affixed appliances 720, and a wire 730 mechanically coupled to the affixed appliances 720. According to this embodiment, various types of affixed appliances 720 are provided. Affixed appliances 720 include a buccal tube 720*a* and a bracket 720*b*. Buccal tube 720*a* includes a hook that may be used, for example, for coupling to a band (not illustrated). Similar to the embodiment discussed above with reference to FIG. 6, tracking template 700 includes a plurality of tooth-receiving cavities for covering surfaces of teeth 710 extending from a cusp of teeth 710 (e.g., a contact surface) to a location on teeth 710 proximate to wire 730. An edge of the tooth-receiving cavities closest to affixed appliances 720 may be contoured to the shape of affixed appliances 720 such that the tooth-receiving cavities are formed around affixed appliances 720 but not over affixed appliances 720. Accordingly, the tooth-receiving cavities may abut edges of the affixed appliances 720. Further, while the tooth-receiving cavities extend to a location on teeth 710 proximate to wire 630, the tooth-receiving cavities do not extend over wire 630. Rather, the tooth-receiving cavities substantially abut wire 630 when disposed over teeth 710. According to some embodiments, tooth-receiving cavities also cover surfaces of teeth, such as tooth 710*a*, that do not have affixed appliances attached thereto.

Although various embodiments and examples have been described with reference to FIG. 7, numerous variations and combinations with reference to other embodiments of the present invention (e.g., those discussed with reference to FIGS. 4A to 4H, FIGS. 5A to 5D, and FIGS. 6A to 6E) are also within the scope of embodiments of the present invention.

Figure 8:
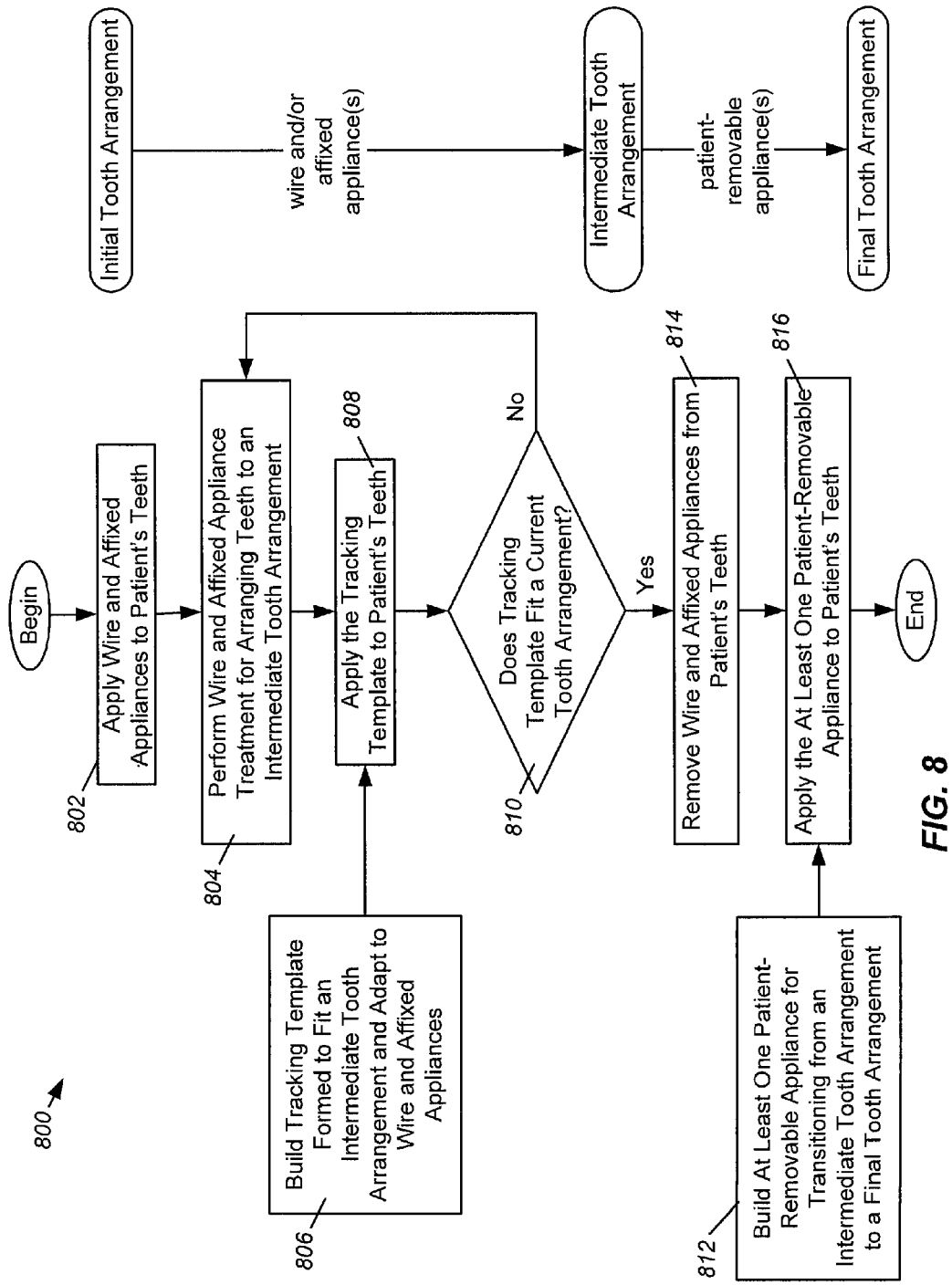
FIG. 8 shows a method for performing an orthodontic treatment in accordance with an embodiment of the present invention.

FIG. 8 shows a method 800 for performing an orthodontic treatment in accordance with an embodiment of the present invention. In operation 802, a wire and affixed appliances are applied to a patient's teeth. For example, the wire and affixed appliances may include the wire and affixed appliances previously discussed. Accordingly, affixed appliances may include brackets for holding or supporting a wire, orthodontic separators (i.e., spacers), a coil spring (e.g., a small spring placed around the archwire to either maintain or increase space between teeth), a tube, a band (e.g., a ring surrounding an anchor molar tooth in the back of the mouth), a tie (e.g., for holding a wire in place), a ligature tie (e.g., a very thin wire wrapped around a bracket holding the archwire into its slot), an expansion appliance (e.g., an appliance placed in the palate used to widen the arch), a hook (e.g., a part of the bracket or band used for attachment of rubber bands), a microchip (e.g., an electronic device that measures the forces that act on a bracket and subsequently, a tooth interface), etc. The wire and affixed appliances may be applied to the patient's teeth while the patient's teeth are in an initial tooth arrangement. In some embodiments, there is no wire provided. Rather, one or more affixed appliances are applied to the patient's teeth.

In operation 804, a wire and affixed appliance treatment is performed for arranging the patient's teeth from the initial tooth arrangement to a planned intermediate tooth arrangement. The intermediate tooth arrangement is predetermined, and may be referred to as a transition arrangement or a target arrangement. That is, at the time the patient's teeth are in the intermediate tooth arrangement, the wire and affixed appliances may be removed and a new treatment may begin. The new treatment may comprise applying at least one patient-removable appliance to the patient's teeth to reposition the teeth from the planned intermediate tooth arrangement to a planned final tooth arrangement. In some embodiments, there is no wire provided. Accordingly, an affixed appliance treatment is performed for arranging the patient's teeth from the initial tooth arrangement to the planned intermediate tooth arrangement.

The wire and affixed appliance treatment may include using wire and bracket planning software, such as Insignia, where the planning software utilizes virtual 3D models of a patient's teeth, a wire, and brackets to assist in designing the treatment plan. The planning software may be utilized before treatment of the patient begins. In some embodiments, the planning software may also be used during treatment; for example, to modify the planned intermediate tooth arrangement. By using such software, a 3D model of a patient's teeth in the intermediate or transition tooth arrangement may be generated prior to (or while) performing the wire and affixed appliance treatment. Further, various aspects of the teeth and wire may be digitally modeled, as may various types of affixed appliances. Accordingly, digital representations of any or all of the patient's teeth (in the initial, intermediate, and/or final tooth arrangement), any or all affixed appliances, and any or all wires may be generated prior to and/or during treatment.

In operation 806, a tracking template is formed. The tracking template is formed to fit over at least a portion of the plurality of patient's teeth in the planned intermediate tooth arrangement without applying a tooth-moving force to the plurality of teeth or the affixed appliances. In some embodiments, the tracking template is adapted to a wire mechanically coupled to the affixed appliances. In such embodiments, the tracking template is formed to fit over at least a portion of the plurality of patient's teeth without interfering with the wire. Any of the tracking templates previously discussed may be formed. For example, where the wire and affixed appliance treatment includes attaching affixed appliances to a lingual or facial surface of a patient's teeth, a tracking template as discussed with reference to FIGS. 3A and 3B may be formed. For another example, where the wire and affixed appliance treatment includes attaching affixed appliances to a lingual surface of a patient's teeth, a tracking template as discussed with reference to FIG. 3C may be formed. For yet another example, any of the tracking templates as discussed with reference to any or all of FIGS. 4 to 7 may be formed.

The tracking template may be formed at any time prior to application of the template (i.e., prior to operation 808). For example, the tracking template may be formed prior to applying the wire and affixed appliances (i.e., operation 802). For another example, the tracking template may be formed while the wire and affixed appliance treatment (i.e., operation 804) is ongoing.

In operation 808, the tracking template formed in operation 806 is applied to the patient's teeth. That is, the orthodontist, patient, or other party or device attempts to fit the tracking template over the patient's teeth. This may include attempting to fit the tracking template over or with at least one of the wire and affixed appliance(s).

In operation 810, a determination is made as to whether the tracking template fits over the patient's teeth. That is, whether the tracking template fits a current tooth arrangement of the patient. If the tracking template fits, then it may be determined that the patient's teeth have been repositioned into the planned intermediate tooth arrangement. As a result, the wire and affixed appliances may be removed (i.e., operation 814) and a different treatment may begin. On the other hand, if the tracking template does not fit, then it may be determined that the patient's teeth have not been repositioned into the planned intermediate tooth arrangement. As a result, wire and affixed appliance treatment is continued (i.e., operation 804) to position the patient's teeth to the intermediate tooth arrangement.

In accordance with an embodiment of the present invention, the tracking template may be formed using a material that is clear or reflective such that the patient's teeth are visible through the tracking template when the tracking template fits the patient's teeth (i.e., when the geometry of the tooth-receiving cavities matches the geometry of the patient's teeth). Accordingly, if the patient's teeth are visible when the tracking template is disposed over the teeth, it may be determined that the tracking template fits over the patient's teeth. On the other hand, if the patient's teeth are not visible when the tracking template is disposed over the teeth, it may be determined that the tracking template does not fit over the patient's teeth.

In accordance with another embodiment of the present invention, a light such as a laser or high-powered fluorescent light may be applied to determine whether the tracking template fits over the patient's teeth. For example, after the tracking template has been positioned over the patient's teeth, a light may be applied to the patient's teeth. A determination may then be made as to whether there are any substantial spaces between the patient's teeth and the tooth-receiving cavities of the tracking template. If substantial spaces exist, it may be determined that the tracking template does not fit over the patient's teeth. On the other hand, if no substantial spaces exist, it may be determined that the tracking template fits over the patient's teeth. As to whether a space is substantial may be determined by the orthodontist or dentist performing the treatment. For example, in some embodiments, a substantial space may be between 1 and 5 micrometers. In other embodiments, a substantial space may be greater than 5 micrometers.

In accordance with yet another embodiment of the present invention, a ground material (e.g., a powdered material) may be disposed within the tooth-receiving cavities of the tracking template prior to positioning the tracking template over the patient's teeth. The ground material may leave a mark on the patient's teeth indicating where the tracking template touches the patient's teeth. Accordingly, after removal of the tracking template, if the patient's teeth are substantially covered with the ground material, it may be determined that the tracking template fits over the patient's teeth. On the other hand, if the patient's teeth are not substantially covered with the ground material, it may be determined that the tracking template does not fit over the patient's teeth. As to whether the teeth are substantially covered by the ground material may be determined by the orthodontist or dentist performing the treatment.

In operation 812, at least one patient-removable orthodontic tooth positioning appliance is formed. The at least one patient-removable appliance may be formed to transition the patient's teeth from the planned intermediate tooth arrangement to a planned final tooth arrangement. One or more of the patient-removable orthodontic tooth positioning appliances 210 previously discussed may be formed.

The at least one patient-removable orthodontic tooth positioning appliance may be formed at any time prior to application of the appliance (i.e., prior to operation 816). For example, the at least one patient-removable orthodontic tooth positioning appliance may be formed prior to applying the wire and affixed appliances (i.e., operation 802). For another example, the tracking template may be formed while the wire and affixed appliance treatment (i.e., operation 804) is ongoing.

In operation 814, the wire and affixed appliances are removed. These devices are removed in response to determining that the tracking template fits a patient's current tooth arrangement. This includes removing any or all of wire and affixed appliances. In some embodiments, one or more affixed appliances may remain attached to one or more teeth. The remaining affixed appliances may then be used, for example, to aid the patient-removable appliance(s) in positioning or repositioning the patient's teeth. In such a case, the patient-removable appliance(s) will be formed to engage the remaining affixed appliances and apply tooth-moving forces via the remaining affixed appliances. In other embodiments, the remaining affixed appliances may be used for other purposes. In such a case, the patient-removable appliance(s) may or may not be formed to engage the remaining affixed appliances.

In operation 816, the at least one patient-removable orthodontic tooth positioning appliance is applied to the patient's teeth. The at least one patient-removable appliance may function to transition the patient's teeth from the planned intermediate tooth arrangement to a planned final tooth arrangement. One or more of the patient-removable orthodontic tooth positioning appliances 210 previously formed (i.e., formed in operation 812) may be applied. As a result of applying the one or more patient-removable orthodontic tooth positioning appliances, the patient's teeth should be repositioned into the final tooth arrangement.

It should be appreciated that the specific operations illustrated in FIG. 8 provide a particular method for performing an orthodontic treatment, according to certain embodiments of the present invention. Other sequences of operations may also be performed according to alternative embodiments. For example, alternative embodiments of the present invention may perform the operations outlined above in a different order. Moreover, the individual operations illustrated in FIG. 8 may include multiple sub-operations that may be performed in various sequences as appropriate to the individual operation. Furthermore, additional operations may be added or existing steps removed depending on the particular applications. One of ordinary skill in the art would recognize and appreciate many variations, modifications, and alternatives.

Figure 9A:
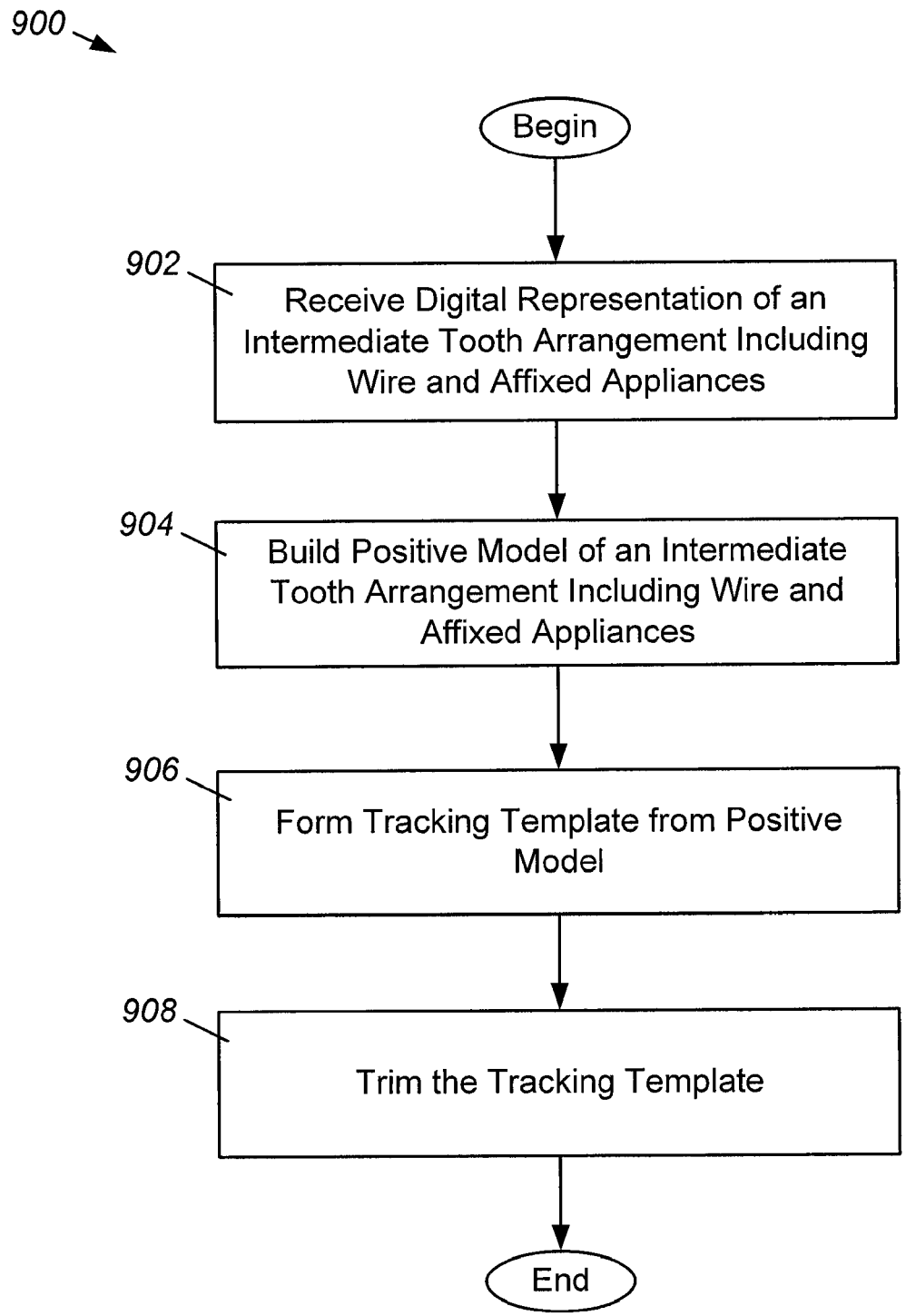
FIG. 9A illustrates a method for fabricating a tracking template in accordance with a first embodiment.

FIG. 9A illustrates a method 900 for fabricating a tracking template in accordance with a first embodiment. It should be appreciated that method 900 can be practiced in a variety of ways. For example, method 900 can be computer implemented and employ three-dimensional modeling representations and techniques.

In operation 902, a digital representation of a patient's teeth in the intermediate tooth arrangement is received. In one embodiment, the received digital representation includes a digital representation of at least one of a wire and affixed appliance(s) as previously discussed. In another embodiment, the received digital representation is modified to include at least one of a wire and affixed appliance(s) as previously discussed. In another embodiment, the digital representation is originally generated and sent from wire and bracket planning software, such as Insignia. In yet another embodiment, the digital representation is obtained from scanning the patient's teeth and subsequently modifying the scanned representation to form the intermediate tooth arrangement.

One of more teeth in the received digital representation may optionally be modified. This optional modification can include any number of the teeth, from one to all. A wide range of modifications are possible. For example, the size of any number of teeth can be scaled by a desired amount. By decreasing the size of a tooth in the representation, the resulting tooth-receiving cavity for the tooth in the tracking template will be smaller than the patient's actual tooth, thereby producing increased interference/contact forces between the cavity and the tooth. Similarly, increasing the size of a tooth in the representation will result in a cavity larger than the patient's actual tooth, thereby producing decreased contact between the cavity and the tooth.

Other portions of the digital representation may also be optionally modified. For example, the wire and/or affixed appliances may be modified. One of these elements may be modified if it is known that the element (e.g., the wire and/or affixed appliance) will be modified prior to application of the tracking template. For example, if a tracking template is to be applied after removal of an affixed appliance, the affixed appliance may be removed from the digital representation.

In operation 904, a positive model of the intermediate tooth arrangement including at least one of wire and affixed appliance(s) may be formed. The positive model may be formed using the received digital representation. The positive model may be a physical model/mold corresponding to the digital representation. According to some embodiments, modifications as discussed above with respect to the digital representation may be made to the positive model instead of to the digital representation.

In operation 906, a tracking template is formed from the positive model. According to one embodiment, the tracking template may be formed by thermally forming and curing a sheet of polymeric material over the positive model. The material used to form the tracking template should be stiff enough when cured so that the template will not flex over the patient's teeth that still need to be moved to the intermediate tooth arrangement. On the other hand, the material used to form the tracking template should not be so stiff that the template will never fit over the patient's teeth. Examples of specific types of material which may be used for the tracking template include any suitable polymer material, including an elastomeric polymeric material such as Tru-Tain 0.03 in.

thermal forming dental material manufactured by Tru-Tain Plastics of Rochester, Minn., and/or a thermoplastic polyurethane material such as Estane manufactured by Lubrizol of Wickliffe, Ohio, and/or a polycarbonate material such as Lexan manufactured by Saudi Basic Industries Corp. of Riyadh, Saudi Arabia, and/or a polyester or copolyester material such as Eastar manufactured by Eastman Corp. of Kingsport, Tenn., and/or a thermoplastic polyolefin material such as Engage manufactured by The Dow Chemical Co. of Midland, Mich.

In operation 908, the tracking template is trimmed. Various techniques can be used to trim the tracking template formed in operation 906 so as to create the desired shape while leaving smooth edges. For example, the tracking template may be trimmed using a machining tool, such as a 5-axis CNC machining device manufactured by Haas Automation, Inc., of Oxnard, Calif. For another example, the tracking template may be manually trimmed using scissors, knives, or other cutting tools. The tracking template may be trimmed so as to result in any of the tracking templates previously discussed.

It should be appreciated that the specific operations illustrated in FIG. 9A provide a particular method for fabricating a tracking template, according to certain embodiments of the present invention. Other sequences of operations may also be performed according to alternative embodiments. For example, alternative embodiments of the present invention may perform the operations outlined above in a different order. Moreover, the individual operations illustrated in FIG. 9A may include multiple sub-operations that may be performed in various sequences as appropriate to the individual operation. Furthermore, additional operations may be added or existing steps removed depending on the particular applications. One of ordinary skill in the art would recognize and appreciate many variations, modifications, and alternatives.

Figure 9B:
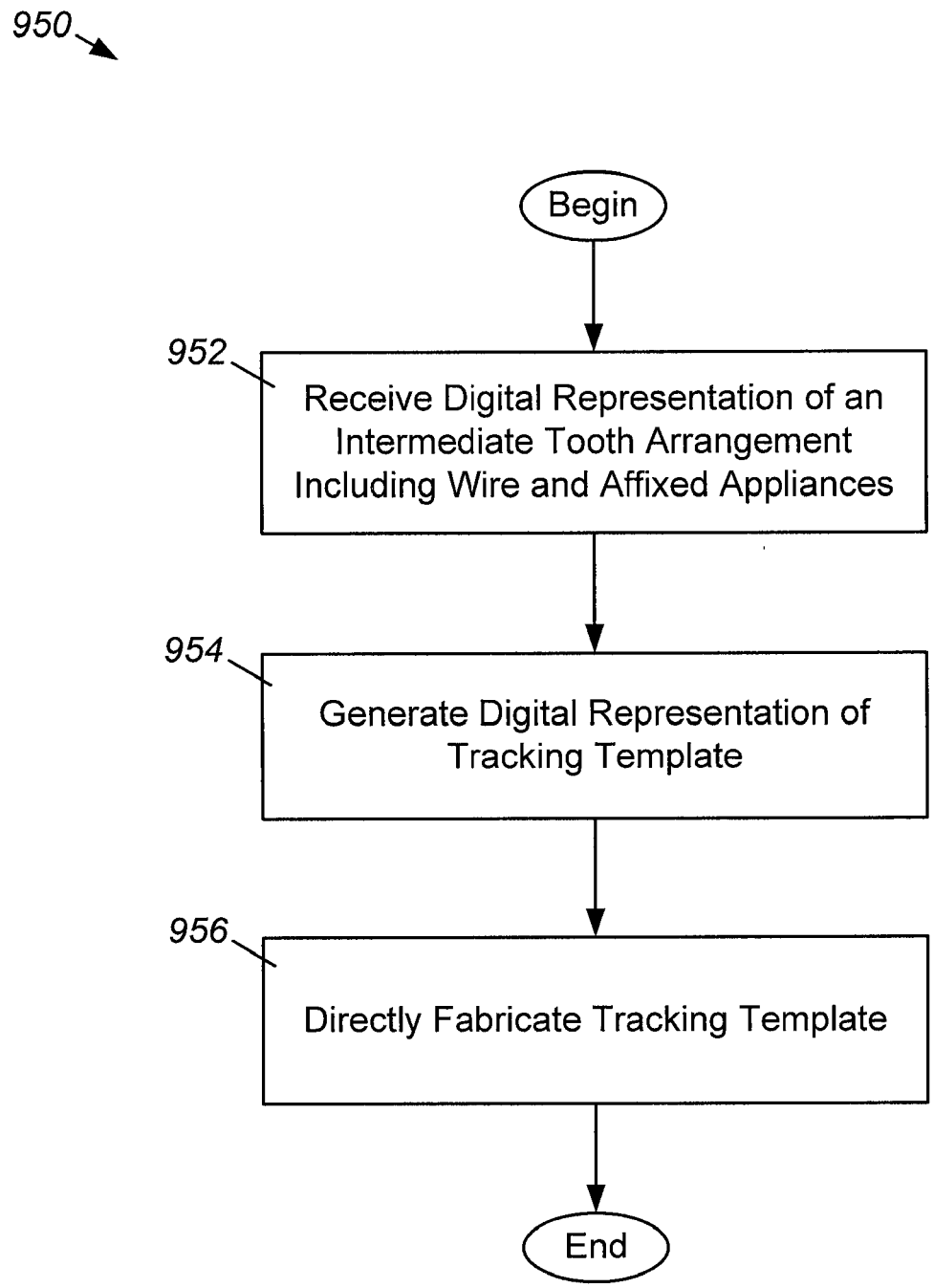
FIG. 9B illustrates a method for fabricating a tracking template in accordance with a second embodiment.

FIG. 9B illustrates a method 950 for fabricating a tracking template in accordance with a second embodiment. It should be appreciated that method 950 can be practiced in a variety of ways. For example, method 950 can be computer implemented and employ three-dimensional modeling representations and techniques.

In operation 952, a digital representation of a patient's teeth in the intermediate tooth arrangement is received. The digital representation received may be the same as that discussed above with reference to operation 902, and may be optionally modified as also discussed above with reference to operation 902.

In operation 954, a digital representation of a tracking template is generated. The digital representation of the tracking template may be generated using the digital representation of the patient's teeth received in operation 952 The digital representation of the tracking template may be adapted to fit a digital representation of at least one of the wire and affixed appliance(s), such that the digital representation is a representation of any of the tracking templates previously discussed.

In operation 956, the tracking template is directly fabricated. Various known manufacturing processes can be used to directly fabricate the tracking template using the digital representation generated in operation 954. For example, the tracking template may be formed by a stereo-lithography fabrication machine, where resin is selectively hardened in the shape of the tracking template.

It should be appreciated that the specific operations illustrated in FIG. 9B provide a particular method for fabricating a tracking template, according to certain embodiments of the present invention. Other sequences of operations may also be performed according to alternative embodiments. For example, alternative embodiments of the present invention may perform the operations outlined above in a different order. Moreover, the individual operations illustrated in FIG. 9B may include multiple sub-operations that may be performed in various sequences as appropriate to the individual operation. Furthermore, additional operations may be added or existing steps removed depending on the particular applications. One of ordinary skill in the art would recognize and appreciate many variations, modifications, and alternatives.

Figure 10:
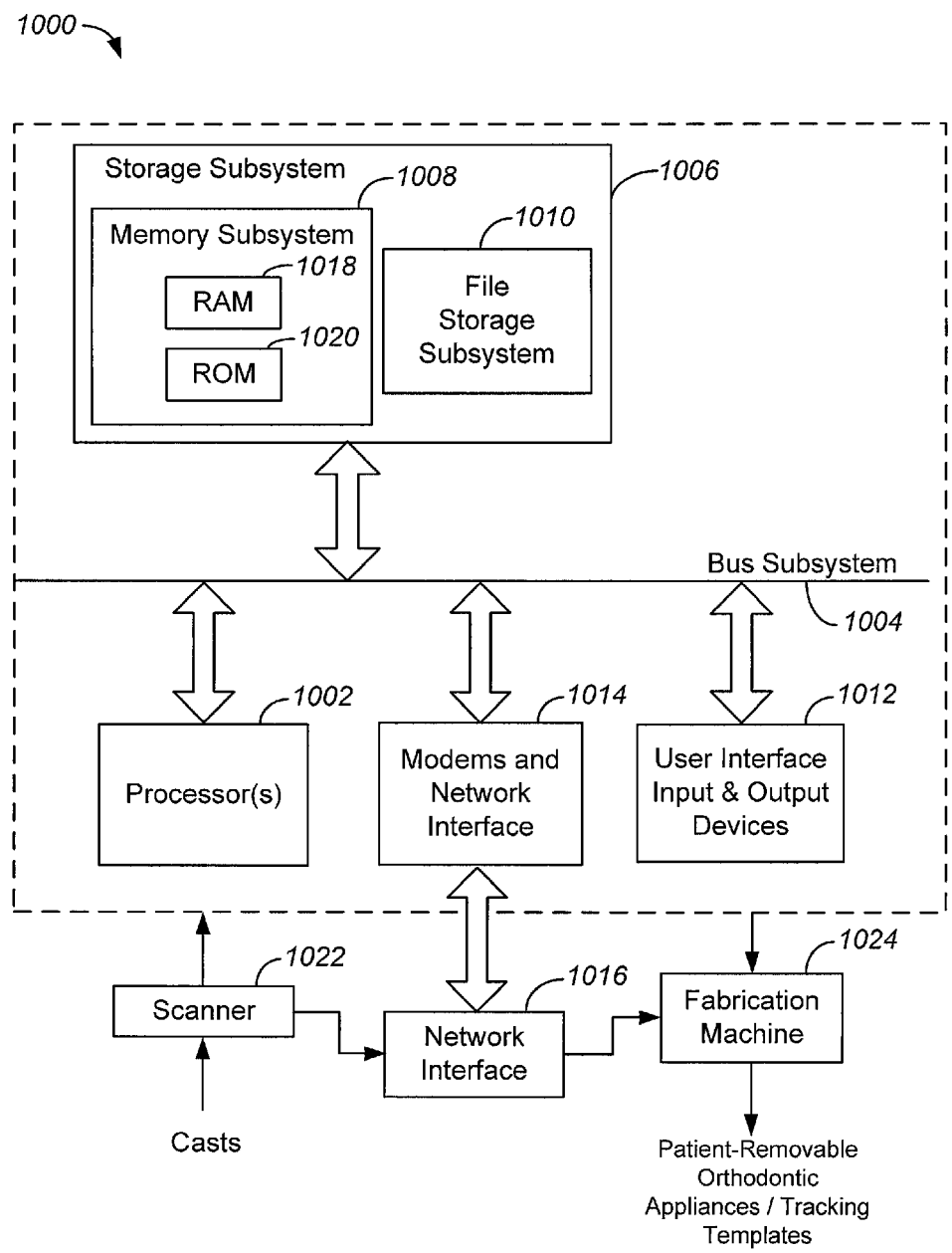
FIG. 10 is a simplified block diagram of a data processing system embodying embodiments of the present invention.

FIG. 10 is a simplified block diagram of a data processing system 1000 embodying embodiments of the present invention. Data processing system 1000 typically includes at least one processor 1002 which communicates with a number of peripheral devices via a bus subsystem 1004. These peripheral devices typically include a storage subsystem 1006 (memory subsystem 1008 and file storage subsystem 1010), a set of user interface input and output devices 1012, and an interface to outside networks 1014, including the public switched telephone network. This interface is shown schematically as "Modems and Network Interface" block 1014, and is coupled to corresponding interface devices in other data processing systems via a communication network interface 1016. Data processing system 1000 could be a terminal or a low-end personal computer or a high-end personal computer, workstation, or mainframe.

The user interface input devices typically include a keyboard and may further include a pointing device and a scanner. The pointing device may be an indirect pointing device such as a mouse, trackball, touchpad, or graphics tablet, or a direct pointing device such as a touch screen incorporated into the display. Other types of user interface input devices, such as voice recognition systems, are also possible.

User interface output devices typically include a printer and a display subsystem, which includes a display controller and a display device coupled to the controller. The display device may be a cathode ray tube (CRT), a flat-panel device such as a liquid crystal display (LCD), or a projection device. The display subsystem may also provide non-visual display such as audio output.

Storage subsystem 1006 maintains the basic programming and data constructs that provide the functionality of embodiments of the present invention. Software modules used to implement the methods discussed above are typically stored in storage subsystem 1006. Storage subsystem 1006 typically comprises memory subsystem 1008 and file storage subsystem 1010.

Memory subsystem 1008 typically includes a number of memories including a main random access memory (RAM) 1018 for storage of instructions and data during program execution and a read only memory (ROM) 1020 in which fixed instructions are stored. In the case of Macintosh-compatible personal computers the ROM would include portions of the operating system; in the case of IBM-compatible personal computers, this would include the BIOS (basic input/output system).

File storage subsystem 1010 provides persistent (non-volatile) storage for program and data files, and typically includes at least one hard disk drive and at least one disk drive (with associated removable media). There may also be other devices such as a CD-ROM drive and optical drives (all with their associated removable media). Additionally, the system may include drives of the type with removable media cartridges. The removable media cartridges may, for example be hard disk cartridges, such as those marketed by Syquest and others, and flexible disk cartridges, such as those marketed by Iomega. One or more of the drives may be located at a remote location, such as in a server on a local area network or at a site on the Internet's World Wide Web.

In this context, the term "bus subsystem" is used generically so as to include any mechanism for letting the various components and subsystems communicate with each other as intended. With the exception of the input devices and the display, the other components need not be at the same physical location. Thus, for example, portions of the file storage system could be connected via various local-area or wide-area network media, including telephone lines. Similarly, the input devices and display need not be at the same location as the processor, although it is anticipated that the present invention will most often be implemented in the context of PCs and workstations.

Bus subsystem 1004 is shown schematically as a single bus, but a typical system has a number of buses such as a local bus and one or more expansion buses (e.g., ADB, SCSI, ISA, EISA, MCA, NuBus, or PCI), as well as serial and parallel ports. Network connections are usually established through a device such as a network adapter on one of these expansion buses or a modem on a serial port. The client computer may be a desktop system or a portable system.

Scanner 1022 is responsible for scanning impressions or casts of the patient's teeth obtained either from the patient or from an orthodontist and providing the scanned digital data set information to data processing system 1000 for further processing. According to some embodiments, canner 1022 may operate to directly scan a patient's teeth and, in some cases, at least one of a wire and affixed attachments. In a distributed environment, scanner 1022 may be located at a remote location and communicate scanned digital data set information to data processing system 1000 via network interface 1016.

Fabrication machine 1024 may fabricate patient-removable orthodontic appliances based on tooth arrangement information received from data processing system 1000. According to some embodiments, fabrication machine 1024 may fabricate the tracking template based on tooth arrangement and, in some cases, wire and/or affixed attachment information received from data processing system 1000. In a distributed environment, fabrication machine 1024 may be located at a remote location and receive data set information from data processing system 1000 via network interface 1016.

One or more structures as described herein may be provided in the form of a kit. For example, a kit may contain one or more of a patient-removable orthodontic appliance or plurality (e.g., set) of patient-removable orthodontic appliances, a tracking template, a wire, an affixed appliance (e.g., a bracket), etc. A tooth-receiving cavity of a patient-removable orthodontic appliance can be treated or altered, e.g., by chemical means, so as to affect a property of the appliance. A kit can be configured for delivery to an intended recipient (e.g., patient, practitioner, etc.) directly or indirectly. A kit can include an object or component provided separated from an appliance, but which is meant to be coupled with another component. For example, bonding material and/or an affixed appliance can be provided.

The software components or functions described in this application may be implemented as software code to be executed by one or more processors using any suitable computer language such as, for example, Java, C++ or Perl using, for example, conventional or object-oriented techniques. The software code may be stored as a series of instructions, or commands on a computer-readable medium, such as a random access memory (RAM), a read-only memory (ROM), a magnetic medium such as a hard-drive or a floppy disk, or an optical medium such as a CD-ROM. Any such computer-readable medium may also reside on or within a single computational apparatus, and may be present on or within different computational apparatuses within a system or network.

The present invention can be implemented in the form of control logic in software or hardware or a combination of both. The control logic may be stored in an information storage medium as a plurality of instructions adapted to direct an information processing device to perform a set of steps disclosed in embodiments of the present invention. Based on the disclosure and teachings provided herein, a person of ordinary skill in the art will appreciate other ways and/or methods to implement the present invention.

The use of the terms "a" and "an" and "the" and similar referents in the context of describing embodiments (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments and does not pose a limitation on the scope unless otherwise claimed. No language in the specification should be construed as indicating any non-claimed element as essential to the practice of at least one embodiment.

Preferred embodiments are described herein, including the best mode known to the inventors. Variations of those preferred embodiments may become apparent to those of ordinary skill in the art upon reading the foregoing description. The inventors expect skilled artisans to employ such variations as appropriate, and the inventors intend for embodiments to be constructed otherwise than as specifically described herein. Accordingly, suitable embodiments include all modifications and equivalents of the subject matter recited in the claims appended hereto as permitted by applicable law. Moreover, any combination of the above-described elements in all possible variations thereof is contemplated as being incorporated into some suitable embodiment unless otherwise indicated herein or otherwise clearly contradicted by context. The scope of the invention should, therefore, be determined not with reference to the above description, but instead should be determined with reference to the pending claims along with their full scope or equivalents.

What is claimed is:

1. A method of fabricating a tracking template for a patient wearing at least one affixed appliance attached to at least one tooth of a plurality of teeth, the method comprising:

receiving a digital representation of the plurality of teeth in a planned intermediate tooth arrangement, the digital representation including a digital representation of the at least one affixed appliance, the at least one fixed appliance comprising at least one bracket mounted on the at least one tooth and a wire coupled to the at least one bracket; and forming a tracking template using the received digital representation, the tracking template comprising a shell defining a plurality of tooth-receiving cavities shaped to fit over at least a portion of the plurality of teeth in the planned intermediate tooth arrangement without applying a tooth-moving force to the plurality of teeth or the at least one affixed appliance, a first shell portion of the tracking template extending from a cusp of the at least one tooth and ends at a surface of the at least one affixed appliance closest to the cusp of the at least one tooth, a second shell portion extends at least partially over the wire.

2. The method of claim 1, wherein forming the tracking template comprises:

building a positive model of the plurality of teeth in the planned intermediate tooth arrangement using the received digital representation, the positive model including the at least one affixed appliance; and forming the tracking template from the positive model.

3. The method of claim 2, wherein forming the tracking template further comprises trimming the tracking template.

4. The method of claim 1, wherein forming the tracking template comprises directly fabricating the tracking template using the digital representation.

5. The method of claim 4, wherein the tracking template is directly fabricated using a stereo-lithography fabrication machine.

6. The method of claim 1, wherein forming the tracking template comprises:

generating a digital representation of the tracking template using the received digital representation; and fabricating the tracking template from the digital representation of the tracking template.

7. The method of claim 1, further comprising modifying the digital representation before forming the tracking template.

8. The method of claim 7, wherein modifying the digital representation comprises increasing or decreasing a size of one or more teeth of the plurality of teeth.

9. The method of claim 1, wherein the digital representation is received from a computing device executing wire and bracket planning software.

10. The method of claim 9, wherein the wire and bracket planning software is configured to generate a treatment plan for moving the plurality of teeth from an initial tooth arrangement to the planned intermediate tooth arrangement using the at least one affixed appliance.

11. The method of claim 1, wherein the at least one affixed appliance further comprises one or more of; brackets, orthodontic separators, coil springs, tubes, bands, ties, ligature ties, expansion appliances, hooks, or microchips.

12. The method of claim 1, wherein the first shell portion of the tracking template comprises one or more appliance-receiving surfaces arranged to abut an edge of the at least one bracket.

13. The method of claim 12, wherein the one or more appliance-receiving surfaces are shaped to conform to at least a portion of the at least one bracket.

14. A method of fabricating a tracking template for a patient wearing at least one affixed appliance attached to at least one tooth of a plurality of teeth, the method comprising:

receiving a digital representation of the plurality of teeth in a planned intermediate tooth arrangement, the digital representation including a digital representation of the at least one affixed appliance, the at least one fixed appliance comprising at least one bracket mounted on the at least one tooth and a wire coupled to the at least one bracket; and forming a tracking template using the received digital representation, the tracking template comprising a shell defining a plurality of tooth-receiving cavities shaped to fit over at least a portion of the plurality of teeth in the planned intermediate tooth arrangement without applying a tooth-moving force to the plurality of teeth or the at least one affixed appliance, a first shell portion of the tracking template extending from a cusp of the at least one tooth and ends at a surface of the at least one affixed appliance closest to the cusp of the at least one tooth, a second shell portion of the tracking template extends from a cusp of the at least one tooth to one or more wire-receiving surfaces arranged to abut a surface of the wire.

15. The method of claim 14, wherein the one or more wire-receiving surfaces are shaped to conform to at least a portion of the wire.

16. The method of claim 14, wherein forming the tracking template comprises:

building a positive model of the plurality of teeth in the planned intermediate tooth arrangement using the received digital representation, the positive model including the at least one affixed appliance; and forming the tracking template from the positive model.

17. The method of claim 14, wherein forming the tracking template comprises directly fabricating the tracking template using the digital representation.

18. The method of claim 14, wherein forming the tracking template comprises:

generating a digital representation of the tracking template using the received digital representation; and fabricating the tracking template from the digital representation of the tracking template.

19. The method of claim 14, further comprising modifying the digital representation before forming the tracking template.

20. The method of claim 14, wherein the digital representation is received from a computing device executing wire and bracket planning software.

* * * * *